(12) United States Patent
Kim et al.

(10) Patent No.: US 12,239,436 B2
(45) Date of Patent: Mar. 4, 2025

(54) MODE CONTROL METHOD AND DEVICE USING MOVEMENT PATTERN CHARACTERISTICS OF USER

(71) Applicant: Samsung Electronics Co., Ltd., Gyeonggi-do (KR)

(72) Inventors: Hyeonseong Kim, Gyeonggi-do (KR); Jeonggwan Kang, Gyeonggi-do (KR); Seunghyuck Shin, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 602 days.

(21) Appl. No.: 17/511,783

(22) Filed: Oct. 27, 2021

(65) Prior Publication Data

US 2022/0047185 A1    Feb. 17, 2022

Related U.S. Application Data

(63) Continuation of application No. PCT/KR2020/000867, filed on Jan. 17, 2020.

(30) Foreign Application Priority Data

May 24, 2019    (KR) ........................ 10-2019-0061324

(51) Int. Cl.
*A61B 5/11* (2006.01)
*A61B 5/00* (2006.01)

(52) U.S. Cl.
CPC ........... *A61B 5/1118* (2013.01); *A61B 5/1123* (2013.01); *A61B 5/7264* (2013.01); *A61B 2562/0219* (2013.01)

(58) Field of Classification Search
CPC ............................ A61B 5/1118; A61B 5/1123
See application file for complete search history.

(56) References Cited

U.S. PATENT DOCUMENTS

| | | | |
|---|---|---|---|
| 8,036,850 B2 | 10/2011 | Kulach et al. | |
| 8,543,185 B2 | 9/2013 | Yuen et al. | |
| 8,784,271 B2 | 7/2014 | Brumback et al. | |
| 10,973,440 B1 * | 4/2021 | Martin | G06T 13/40 |

(Continued)

FOREIGN PATENT DOCUMENTS

| | | |
|---|---|---|
| JP | 6457346 B2 | 1/2019 |
| KR | 10-2011-0072328 A | 6/2011 |

(Continued)

OTHER PUBLICATIONS

Korean Office Action dated Nov. 27, 2024.

*Primary Examiner* — Mark A Connolly
(74) *Attorney, Agent, or Firm* — Cha & Reiter, LLC

(57) ABSTRACT

Disclosed in certain embodiments is a device including a sensor module, a display, a memory and a processor. The processor may be configured to obtain sensing data from the sensor module, analyze the movement pattern of a user on the basis of the obtained sensing data, estimate movement characteristic information on the basis of the analysis result of the movement pattern, identify the operation mode of the electronic device on the basis of the movement characteristic information, and analyze activity information about the user on the basis of the identified operation mode so as to display same using the display. A method thereof is also disclosed and various other embodiments are also possible.

13 Claims, 18 Drawing Sheets

(56) References Cited

U.S. PATENT DOCUMENTS

| | | |
|---|---|---|
| 2011/0146396 A1 | 6/2011 | Kim et al. |
| 2014/0180033 A1 * | 6/2014 | Altini |
| 2016/0220808 A1 * | 8/2016 | Hyde .................. A61B 5/6804 |
| 2017/0347885 A1 | 12/2017 | Tan et al. |
| 2018/0020953 A1 | 1/2018 | Li et al. |

FOREIGN PATENT DOCUMENTS

| | | |
|---|---|---|
| KR | 10-1440362 B1 | 9/2014 |
| KR | 10-2018-0003112 A | 1/2018 |
| KR | 10-2018-0104881 A | 9/2018 |
| KR | 10-2019-0016753 A | 2/2019 |

* cited by examiner

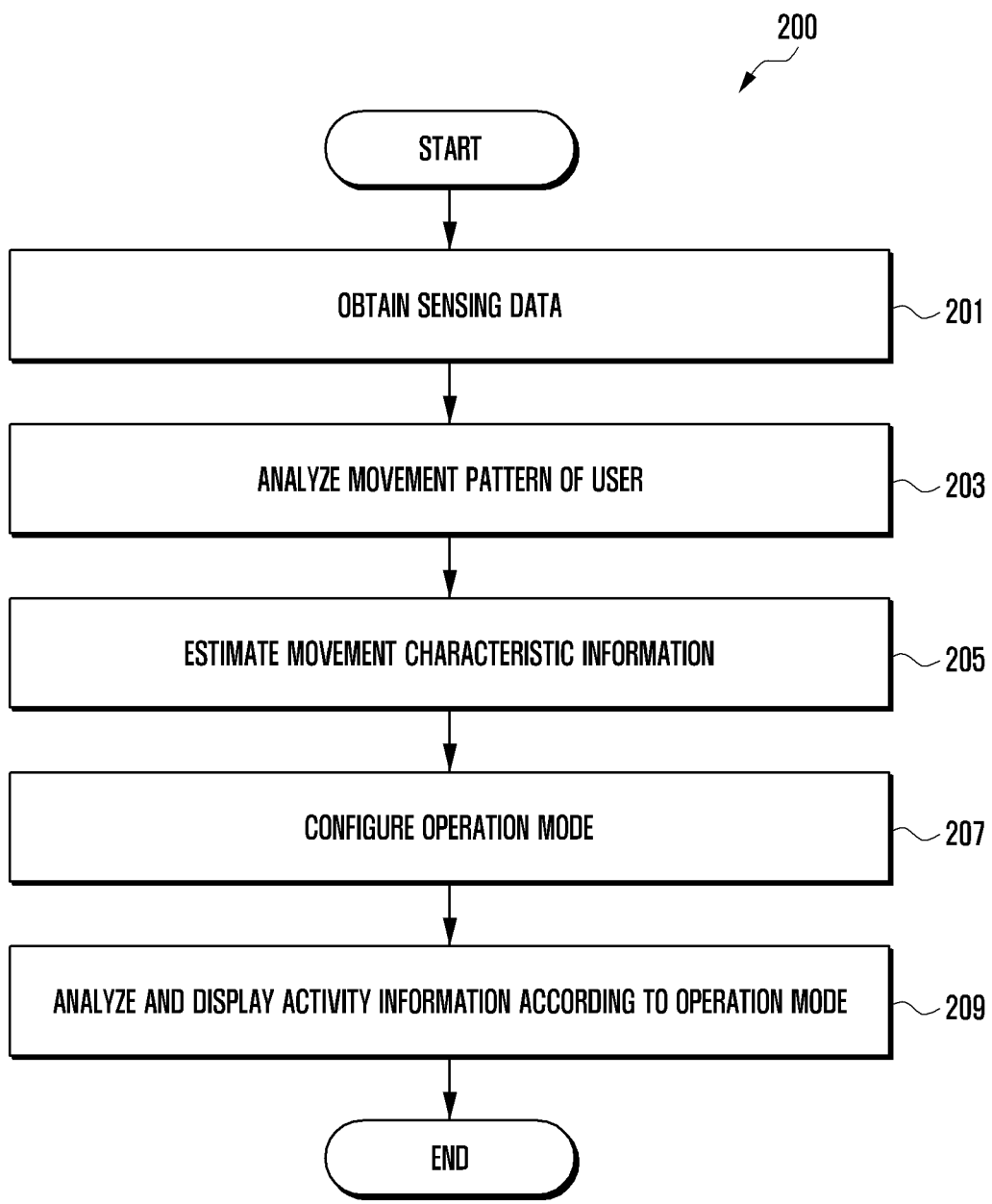

(450)

(510)

FIG. 9
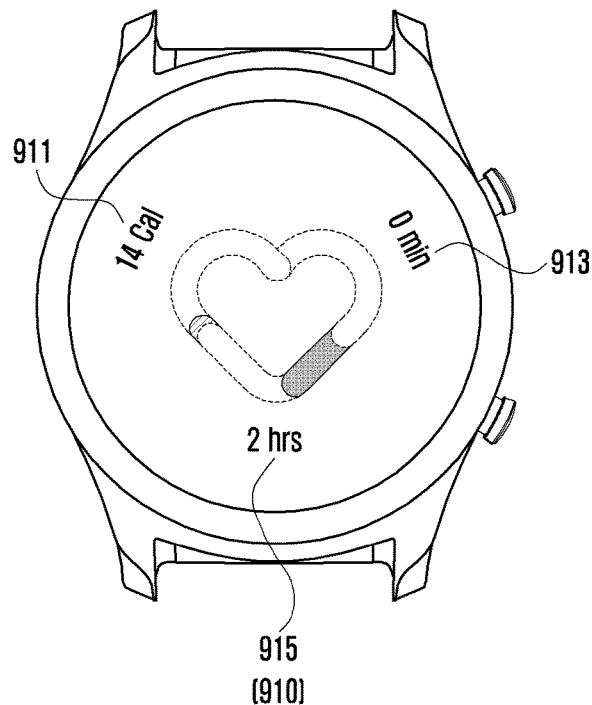
(910)
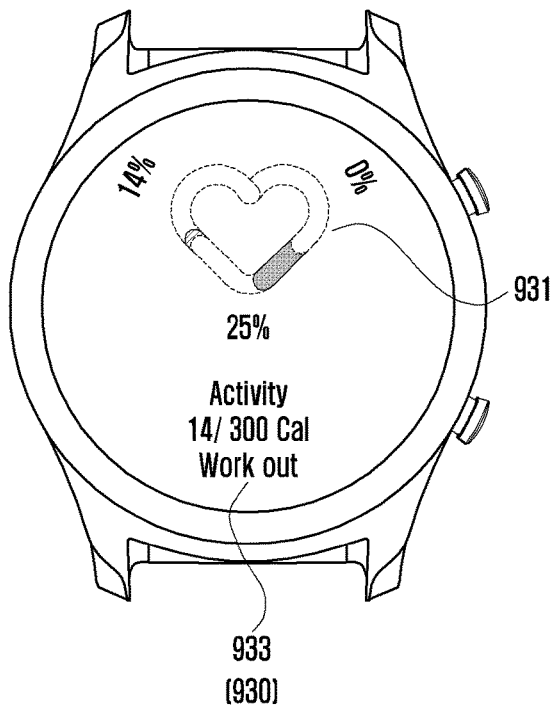
(930)
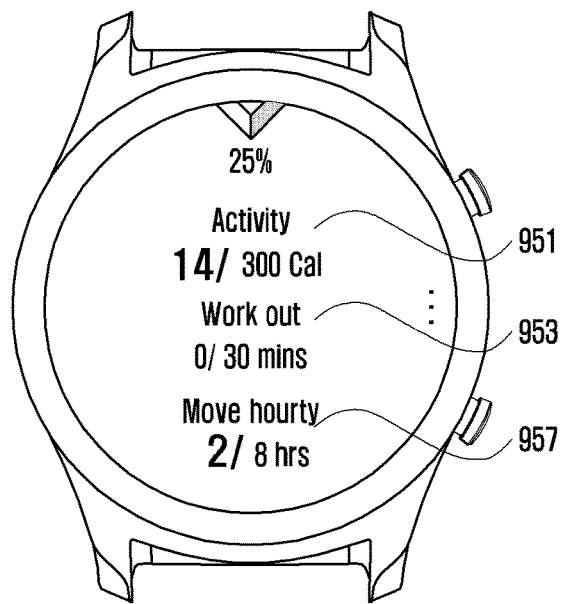
(950)
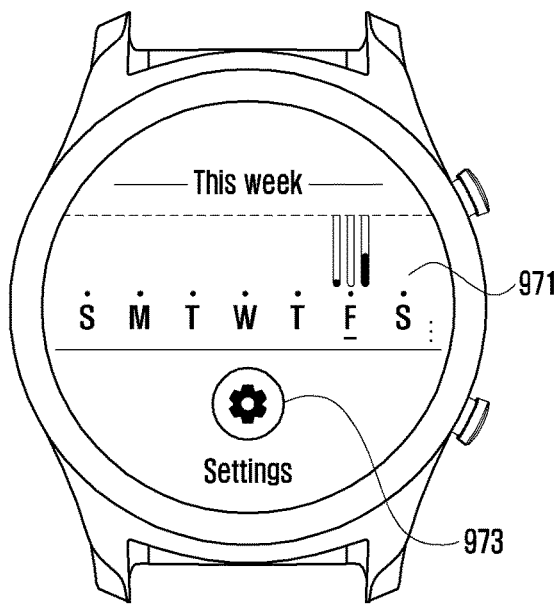
(970)

MODE CONTROL METHOD AND DEVICE USING MOVEMENT PATTERN CHARACTERISTICS OF USER

CROSS-REFERENCE TO RELATED APPLICATION(S)

This application is a continuation of International Application No. PCT/KR2020/000867, filed on Jan. 17, 2020, which claims priority to Korean Patent Application No. 10-2019-0061324 filed on May 24, 2019 in the Korean Intellectual Property Office, the disclosures of which are herein incorporated by reference.

TECHNICAL FIELD

Certain embodiments of the instant disclosure generally relate to a mode control method and apparatus using a movement pattern characteristic of a user.

BACKGROUND ART

With the development of digital technologies, various types of electronic devices such as mobile communication terminals, Personal Digital Assistants (PDAs), electronic organizers, smart phones, tablet Personal Computers (PCs), and wearable devices have become widely used. Manufacturers are continuously improving the hardware and/or software of these electronic devices in order to support the various functions of these electronic devices, which are also increasing.

For example, an electronic device such as the wearable device can contact (or can be worn on) a user's body and may be provided in various forms such as, for example, a smart watch, smart glasses, and a smart band. The wearable device may collect and analyze various pieces of information (for example, biometric information or activity information) of the user and provide various functions (for example, displaying health information) to the user.

When providing a function on the basis of the collected information, the wearable device may inconvenience the user because the wearable device may recognize an activity based on the collected information, however the recognized activity may not be one that is intended by the user.

SUMMARY

Certain embodiments disclosed herein may relate to methods and apparatuses for estimating a pattern characteristic according to movement of a user to automatically switch an operation mode of the electronic device and collecting and providing activity information according to the operation mode.

An electronic device according to an embodiment includes a sensor module, a display, a memory, and a processor, wherein the processor is configured to obtain sensing data from the sensor module, analyze a movement pattern of a user, based on the obtained sensing data, estimate movement characteristic information, based on a result of the analysis of the movement pattern, identify an operation mode of the electronic device, based on the movement characteristic information, and analyze activity information of the user, based on the identified operation mode to display the activity information using the display.

A method of operating an electronic device according to an embodiment includes acquiring sensing data from a sensor module of the electronic device, analyzing a movement pattern of a user, based on the acquired sensing data, estimating movement characteristic information, based on a result of the analysis of the movement pattern, identifying an operation mode of the electronic device, based on the movement characteristic information, and analyzing activity information of the user, based on the identified operation mode to display the activity information using a display of the electronic device.

According to certain embodiments, it is possible to increase user convenience by estimating a pattern characteristic according to user movement and automatically switching (or changing) an operation mode of the electronic device.

According to certain embodiments, it is possible to display activity information suitable for a user movement condition by collecting different pieces of information according to the operation mode of the electronic device as activity information.

According to certain embodiments, it is possible to intuitively provide information according to a user state by displaying activity information differently according to a change in walking pattern.

According to certain embodiments, it is possible to display different pieces of activity information according to a use history for the user even in the same operation mode by displaying activity information differently on the basis of the use history.

BRIEF DESCRIPTION OF DRAWINGS

FIG. 2 is a flowchart 200 illustrating a method of operating an electronic device according to an embodiment.

FIG. 9 is a diagram illustrating an example of a user interface for displaying activity information in an electronic device according to an embodiment.

DETAILED DESCRIPTION

Figure 1:
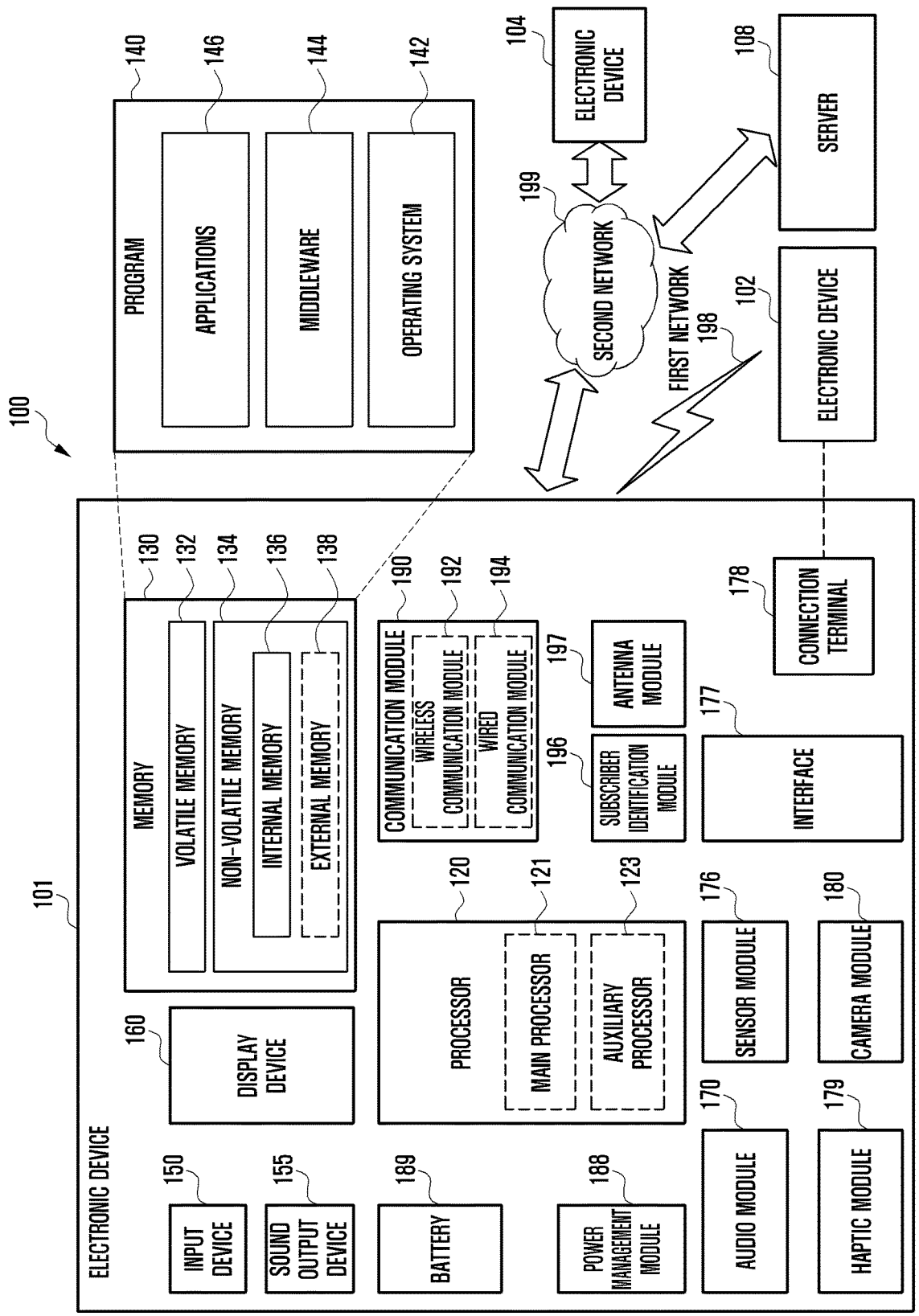
FIG. 1 is a block diagram illustrating an electronic device 101 within a network environment 100 according to various embodiments.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector), The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

An electronic device (for example, the electronic device 101 of FIG. 1) according to an embodiment may include a sensor module (for example, the sensor module 176 of FIG. 1), a display (for example, the display device 160 of FIG. 1), a memory (for example, the memory 130 of FIG. 1), and a processor (for example, the processor 120 of FIG. 1), wherein the processor may be configured to obtain sensing data from the sensor module, analyze a movement pattern of a user on the basis of the obtained sensing data, estimate movement characteristic information on the basis of a result of the analysis of the movement pattern, identify an operation mode of the electronic device on the basis of the movement characteristic information, and analyze activity information of the user on the basis of the identified operation mode to display the activity information using the display. The processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed under the provisions of 35 U.S.C. 112(f), unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

The movement pattern may include a walking pattern or a stroke pattern, and the processor may be configured to extract a pattern characteristic from the sensing data obtained for a predetermined time and identify whether the extracted pattern characteristic corresponds to at least one of the walking pattern or the stroke pattern.

The processor may be configured to analyze the walking pattern and identify the operation mode of the electronic device as at least one a first operation mode, a second operation mode, or a third operation mode.

The processor may be configured to calculate a left/right symmetry level, an up/down symmetry level, or a regularity level by analyzing the walking pattern and identify the operation mode of the electronic device as at least one the first operation mode, the second operation mode, or the third operation mode on the basis of at least one of the calculated left/right symmetry level, up/down symmetry level, or regularity level.

When the left/right symmetry level, the up/down symmetry level, or the regularity level exceeds a reference value, the processor may be configured to identify the operation mode of the electronic device as the first operation mode.

When the left/right symmetry level, the up/down symmetry level, or the regularity level is equal to or smaller than a reference value, the processor may be configured to identify the operation mode of the electronic device as the second operation mode or the third operation mode.

The electronic device may further include a communication module (for example, the communication module 190 of FIG. 1), wherein the processor may be configured to identify whether there is a connection with an external device corresponding to a waling assist device through the communication module, identify the operation mode of the electronic device as the second operation mode when there is no connection with the external device, and identify the operation mode of the electronic device as the third operation mode when there is the connection with the external device.

The processor may be configured to calculate at least one of a Ground Contact Time (GCT) signal, x, y, and z values of an acceleration signal, or an acceleration variance value from the obtained sensing data, and analyze the movement pattern on the basis of at least one of the calculated GCT signal, the x, y, and z values of the acceleration signal, or the acceleration variance value.

The processor may be configured to identify at least one of symmetry, regularity, or undulation on the basis of at least one of the GCT signal, the x, y, and z values of the acceleration signal, or the acceleration variance value.

The processor may be configured to control a function engine on the basis of the identified operation mode and collect the activity information using the function engine.

The processor may be configured to determine different parameters for different operation modes of the electronic device and apply a parameter corresponding to the identified operation mode to the activity information.

The processor may be configured to identify a use history of the electronic device and display the activity information on the basis of the identified use history.

The processor may be configured to display different pieces of activity information on the basis of the identified operation mode.

The processor may be configured to analyze a change in the walking pattern of the user on the basis of the obtained sensing data and display different pieces of activity information according to the change in the walking pattern.

The processor may be configured to obtain location information from the communication module and change the operation mode of the electronic device on the basis of the obtained location information.

The processor may be configured to perform clustering on the basis of the location information for a predetermined time, configure a mode control area corresponding to the location information on the basis of a result of the clustering, and store the configured mode control area in the memory.

The processor may be configured to change the operation mode of the electronic device corresponding to the location information, based on at least one of the mode control area stored in the memory or a mode switching history.

FIG. 2 is a flowchart 200 illustrating a method of operating an electronic device according to an embodiment.

Referring to FIG. 2, in operation 201, a processor (for example, the processor 120 of FIG. 1) of an electronic device (for example, the electronic device 101 of FIG. 1) may obtain (or receive) sensing data from a sensor module (for example, the sensor module 176 of FIG. 1). The sensor module 176 may detect an operation state (for example, power or temperature) or an external environment state (for example, user state) and generate an electrical signal or data value corresponding to the detected state. According to an embodiment, the sensor module 176 may include a gesture sensor, a gyro sensor, an atmospheric pressure sensor, a magnetic sensor, an acceleration sensor, a grip sensor, a proximity sensor, a color sensor, an Infrared (IR) sensor, a biometric sensor, a temperature sensor, a humidity sensor, and/or an illumination sensor.

According to an embodiment, the electronic device 101 may have the form of a wearable device. When the electronic device 101 is worn on the user's body, the sensor module 176 may collect data related to movement of the user and transmit the collected data to the processor 120. For example, movement of the user may indicate a movement condition (or activity) such as walking or running. The processor 120 may obtain the sensing data in real time or periodically.

In operation 203, the processor 120 may analyze the movement pattern of the user on the basis of the sensing data. For example, the sensing data may be a value obtained by measuring acceleration by an acceleration sensor (for example, the sensor module 176). The acceleration sensor may process an output signal and measure dynamic force such as acceleration, vibration, or impact of an object (for example, user). Alternatively, the sensing data may be angular speed data obtained by a gyro sensor (for example, the sensor module 176). The gyro sensor may measure location and direction of mechanical motion of a rotating object (for example, the user). The processor 120 may analyze movement pattern on the basis of the sensing data. The movement pattern may indicate the user's motion that is repeatedly generated within a short time (for example, 1 second, 3 seconds, or the like). Analysis of the movement pattern based on the sensing data may determine whether periodic and repeated motion is detected.

In operation 205, the processor 120 may estimate (or predict or analyze) movement characteristic information on the basis of the analyzed movement pattern. The movement pattern may include a waking pattern or a stroke pattern. The walking pattern and the stroke pattern may have different movement trajectories that are repeatedly generated. The processor 120 may estimate the movement characteristic information on the basis of the movement trajectory. Alternatively, the processor 120 may estimate the movement characteristic information on the basis of the movement trajectory and force applied in connection with the movement trajectory.

According to an embodiment, the processor 120 may calculate (or obtain) an acceleration sensor value (or acceleration variance value) or a Ground Contact Time (GCT) signal on the basis of the sensing data measured (or obtained) for a predetermined time. The GCT signal may be a signal indicating the state in which the user's feet are touching the ground. In the GCT signal, a first section in which the acceleration value is 10 may be the state in which the user's right foot touches the ground and a second section in which the acceleration value is 0 may be the state in which a user's left foot touches the ground. The processor 120 may determine a walking pattern when the GCT signal is extracted (or measured) from the acceleration sensor value, and determine a stroke pattern when the GCT signal is not extracted (or measured) from the acceleration sensor value.

The processor 120 may determine symmetry (or symmetry level) on the basis of an interval ratio between the first section and the second section. The symmetry may indicate left/right symmetry of the user's body or left/right movement of the user's body. The processor 120 may determine regularity (or regularity level) of the first section and the second section for a predetermined time. Regularity may indicate regularity of a walking pattern. The processor 120 may determine undulation by using a variance value of acceleration values measured (or obtained) for a predetermined time. Undulation may indicate up/down symmetry of the user's body or up/down movement of the user's body. The processor 120 may estimate movement characteristic information on the basis of at least one of symmetry, regularity, and undulation.

In general, the walking pattern may be measured by a movement trajectory generated by shaking or swinging of hands back and forth when the user is walking. In the case of a user having no difficulty in walking, the movement trajectory is symmetric and regular. For example, in the case of the user having no difficulty in walking, the movement trajectory when the user moves his/her hand from the back to the front may be similar to (or the same as) the movement trajectory when the user moves his/her hand from the front to the back. Similarity between the movement trajectory of the hand from the back to the front and the movement trajectory of the hand from the front to the back indicate a typical walking pattern, one in which for example the user is not holding a heavy object with his/her hand or both hands. The movement trajectory of a user receiving help from an assist device (for example, crutches or a prosthetic leg) to walk may be more asymmetric leftward/rightward or upward/downward than the movement trajectory of the user having no difficulty in walking or may have irregular characteristics.

Further, the stroke pattern may also be measured by movement trajectory when the user is in a wheelchair—the movement of the user's hands to rotate the wheels of the wheelchair may be detected as the movement trajectory. When measuring the stroke pattern, the movement trajectory when the user's hand moves from the back to the front may be different from the movement trajectory when the user's hand moves from the front to the back. When the user moves his/her hand from the back to the front, the user pushes wheels of the wheelchair with his/her hands, and thus the movement trajectory from the top to the bottom may be generated. Further, when the hand having moved to the front is moved to the back, a movement trajectory from the bottom to the top may be generated. In the stroke pattern, the movement trajectory may have left/right or up/down symmetry compared to the walking pattern. The processor 120 may estimate (or predict) whether the movement characteristic information corresponds to the walking pattern or the stroke pattern on the basis of the movement trajectory.

According to an embodiment, in the case of the walking pattern, almost the same (or similar) speeds (or force) may be measured when the user's hand is moved from the back to the front and moved from the front to the back. On the other hand, in the case of the stroke pattern, speed (or force) may be differently measured when the user's hand is moved from the back to the front and moved from the front to the back. In the case of the stroke pattern, force is applied by pushing wheels of the wheelchair with the hand when the user moves his/her hand from the back to the front, and no force may be applied similar to the walking pattern when the user moves his/her hand from the front to the back. The processor 120 may estimate (or predict) whether the movement characteristic information corresponds to the walking pattern or the stroke pattern on the basis of the movement trajectory and force applied in connection with the movement trajectory.

Although it is illustrated that operation 203 and operation 205 are separately performed in drawings, operation 203 and operation 205 may be concurrently performed.

In operation 207, the processor 120 may configure (or determine) a mode (or operation mode) on the basis of the estimated movement characteristic information. The mode (hereinafter, referred to as an "operation mode") may be configured in the electronic device 101 to collect and provide optimal information for the user movement. The processor 120 may identify one operation mode among a first operation mode, a second operation mode, a third operation mode, or a fourth operation mode on the basis of the movement characteristic information. When the movement characteristic information corresponds to the walking pattern, the processor 120 may identify one operation mode among the first operation mode to the third operation mode. When the movement characteristic information corresponds to the stroke pattern, the processor 120 may identify the fourth operation mode. The processor 120 may configure the electronic device 101 to be in the identified operation mode.

For example, the first operation mode may correspond to the user having no difficulty in walking. The user having no difficulty in walking is a typical user and may mean that there is no difficulty in walking or running without an assist device. When the movement characteristic information corresponds to the walking pattern and at least one the symmetry, regularity, or undulation of the walking pattern exceeds a reference value, the processor 120 may identify the first operation mode in accordance with the user using the electronic device 101. The second operation mode may correspond to the user using an assist device such as the crutches or prosthetic leg. The assist device worn or used by the user corresponding to the second operation mode may not include a communication module (for example, wireless communication module). When the movement characteristic information corresponds to the walking pattern, at least one of the symmetry, regularity, or undulation of the walking pattern is equal to or lower than the reference value, and an external device corresponding to the assist device is not connected through the communication module (for example, the communication module 190 of FIG. 1), the processor 120 may identify the second operation mode in accordance with the user using the electronic device 101.

The third operation mode may correspond to the user using an assist device such as a wearable robot. The assist device worn or used by the user corresponding to the third operation mode may include a communication module. The assist device of the user corresponding to the third operation mode may be connected (or paired) with the electronic device 101. After being connected to the assist device, the processor 120 may perform operation 201 to operation 209. When the movement characteristic information corresponds to the walking pattern, at least one of the symmetry, regularity, or undulation of the walking pattern is equal to or lower than the reference value, and an external device corresponding to the assist device is connected through the communication module 190, the processor 120 may identify the third operation mode in accordance with the user using the electronic device 101. The fourth operation mode may correspond to the user in (or using) a wheelchair. When the movement characteristic information corresponds to the stroke pattern, the processor 120 may identify the fourth operation mode in accordance with the user using the electronic device 101.

In operation 209, the processor 120 may analyze and display activity information according to the operation mode configured in the electronic device 101. The processor 120 may collect activity information in different schemes according to the operation mode configured in the electronic device 101 and may differentiate between the collected activity information. The processor 120 may analyze and display the collected activity information. The activity information may include at least one of the number of steps, healthy walking, the number of strokes, running, calories (burned calories), activity time, the number of floors climbed or descended, or an ascended height. An example of collecting different pieces of activity information according to the operation mode may be as shown in [Table 1] below.

TABLE 1

| Operation mode | Calories | Activity time | Number of steps | Number of strokes | Running | Healthy walking | Number of floors climbed or descended | Ascended height |
|---|---|---|---|---|---|---|---|---|
| First mode | O | O | O | X | O | O | O | X |
| Second mode | O | O | O | X | X | X | O | X |
| Third mode | O | O | O | X | X | X | O | X |
| Fourth mode | O | O | X | O | X | X | X | O |

Referring to [Table 1], when the electronic device 101 is configured to be in the first operation mode (or first mode), the processor 120 may collect activity information on the basis of the first operation mode. The activity information based on the first operation mode may include at least one of the calories, the activity time, the number of steps, the healthy walking (or the number of healthy steps), or the number of floors climbed or descended. The calories may be calories burned in by the user's body by the user's walking or running. The processor 120 may calculate the calories on the basis of at least one of the number of steps, the running, or the healthy walking. The activity time may be a time during which at least one of the number of steps, the running, or the healthy walking is performed. The processor 120 may calculate the activity time on the basis of at least one of the number of steps, the running, or the healthy walking. The healthy walking may be measurement of the number of steps for a predetermined time (for example, 5 minutes or 10 minutes).

According to an embodiment, the processor 120 may count the number of movements (for example, the number of steps or the number of strokes) on the basis of the sensing data and calculate user's activity information (or movement information) such as burned calories, activity time, the number of floors climbed or descended, or the ascended height on the basis of the counted number of movements or the sensing data. According to an embodiment, the processor 120 may calculate user's activity information such as the number of floors climbed or descended, or the ascended height by using an acceleration measurement value or an angular speed measurement value. The user's activity information such as burned calories or activity time may not be calculated when the number of movements is counted for time shorter than a predetermined time (for example, 1 minutes, 3 minutes, or 5 minutes), and the user's activity information such as burned calories or activity time may be calculated when the number of movements is counted for a time longer than or equal to the predetermined time (for example, 5 minutes or 10 minutes).

Although the acceleration sensor or the gyro sensor has been described by way of example in order to help understanding of the disclosure, the disclosure is not limited by the description. The processor 120 may count the number of movements or calculate the user's activity information on the basis of sensing data measured by various sensors (for example, a gesture sensor, an atmospheric pressure sensor, a temperature sensor, and a biometric sensor) as well as the acceleration sensor or the gyro sensor.

According to an embodiment, the processor 120 may reduce power consumption due to the control (or performance) of a function engine by controlling the function engine for collecting (or analyzing) the activity information according to the operation mode. The function engine may be a program (or software) used to collect or analyze the activity information. In the first operation mode, the processor 120 may turn off (or deactivate) the function engine for measuring (or calculating) the number of strokes or the ascended height. In the first operation mode, the processor 120 may turn on (or activate) the function engine for measuring (or calculating) at least one of the calories, the activity time, the number of steps, the healthy walking, or the number of floors moved.

When the electronic device 101 is configured to be in the second operation mode (or second mode), the processor 120 may collect activity information on the basis of the second operation mode. The activity information based on the second operation mode may include at least one of the calories, the activity time, the number of steps, or the number of floors climbed or descended. In the second operation mode, the processor 120 may not calculate some pieces of activity information (for example, healthy walking, running, the number of strokes, or the ascended height) because of the particular user body condition in the second mode (i.e. the user is on crutches). In the second operation mode, the processor 120 may activate the function engine for measuring at least one of the calories, the activity time, the number of steps, or the number of floors moved and deactivate the function engine for measuring at least one of the healthy walking, the running, the number of strokes, or the ascended height.

When the electronic device 101 is configured to be in the third operation mode (or third mode), the processor 120 may collect activity information on the basis of the third operation mode. The activity information based on the third operation mode may include at least one of the calories, the activity time, the number of steps, or the number of floors climbed or descended. The activity information based on the third operation mode may be the same as or different form the activity information based on the second operation mode. The processor 120 may receive device information through the communication module (for example, the communication module 190 of FIG. 1) from the assist device and collect activity information related to the third operation mode on the basis of the received device information. In the third operation mode, the processor 120 may not calculate some pieces of activity information (for example, healthy walking, running, the number of strokes, or the ascended height) because of the particular user body condition in the third mode (i.e. the user is wearing a smart assist device). In the third operation mode, the processor 120 may activate the function engine for measuring at least one of the calories, the activity time, the number of steps, or the number of floors moved and turn off the function engine for measuring at least one of the healthy walking, the running, the number of strokes, or the ascended height.

When the electronic device 101 is configured to be in the fourth operation mode (or fourth mode), the processor 120 may collect activity information on the basis of the fourth operation mode. The activity information based on the fourth operation mode may include at least one of the calories, the activity time, the number of strokes, or the ascended height. The processor 120 may measure (or calculate) the number of strokes or the ascended height instead of measuring the number of steps, the healthy walking, and the number of floors climbed or descended. The activity of the user moving while being in the wheelchair may be movement of wheels of the wheelchair rather than walking. Further, the user in the wheelchair can move on inclined surfaces but cannot ascend or descend stairs, and thus the processor 120 may measure the ascended height instead of the number of floors climbed or descended. The processor 120 may not calculate some pieces of activity information (for example, the number of steps, the healthy walking, the running, and the number of floors moved) because of the particular user body condition in the fourth mode (i.e. the user is in a wheelchair). In the fourth operation mode, the processor 120 may activate the function engine for measuring at least one of the calories, the activity time, the number of strokes, or the ascended height and deactivate the function engine for measuring at least one of the number of steps, the healthy walking, the running, the number of floors moved.

According to an embodiment, the processor 120 may collect activity information related to the fourth operation mode differently on the basis of the user's intervention level (or whether the user intervenes) in connection with driving of the wheelchair. For example, the wheelchair may or may not include at least one of an electric module or a communication module. The processor 120 may obtain device information for the wheelchair from the user in advance or receive the device information from the wheelchair. For example, the processor 120 may apply different parameters (or weight values) to the collected activity information in the cases in which the wheelchair can be moved by the electric module without any user intervention.

Figure 3A:
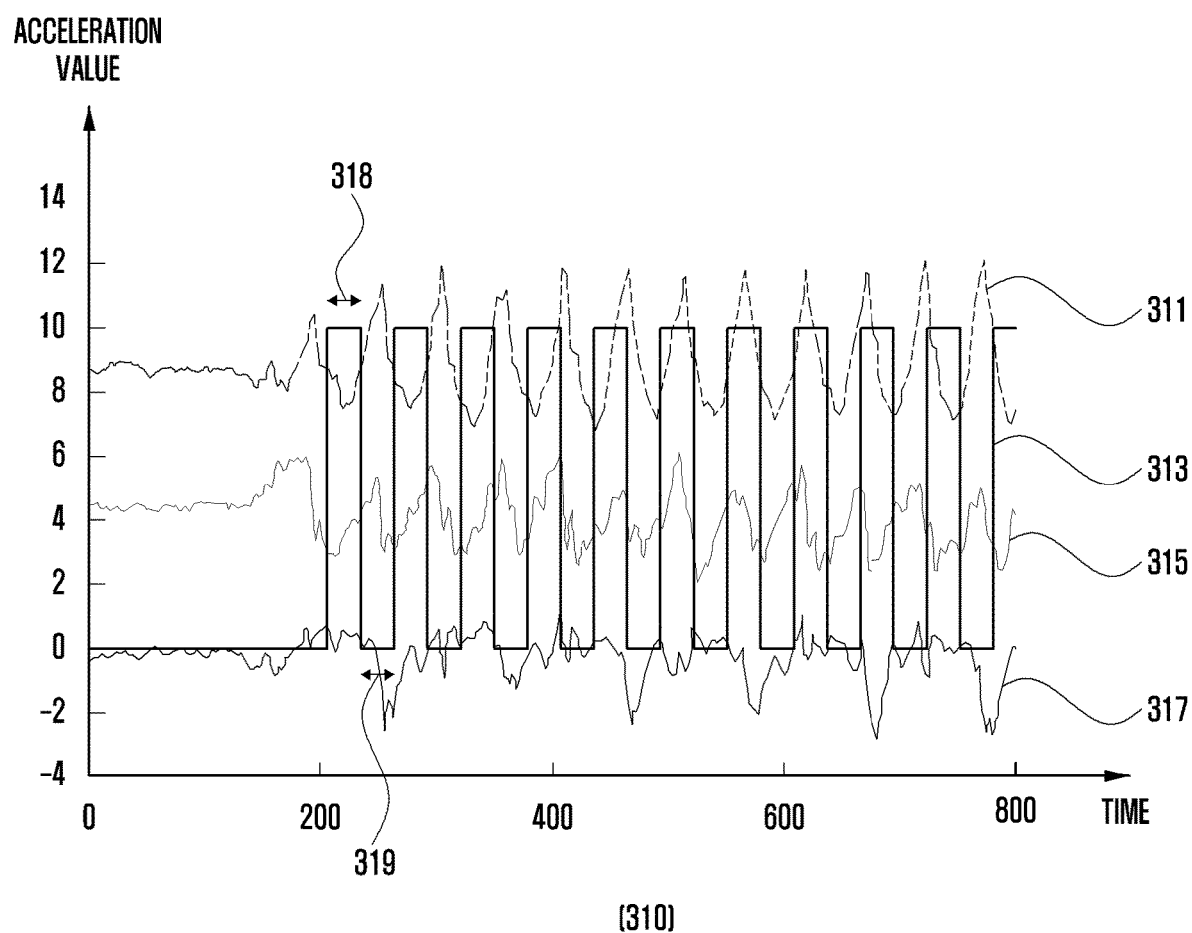
FIGS. 3A and 3B are diagrams illustrating an example of analyzing a walking pattern associated with the first operation mode according to an embodiment.
Figure 3B:
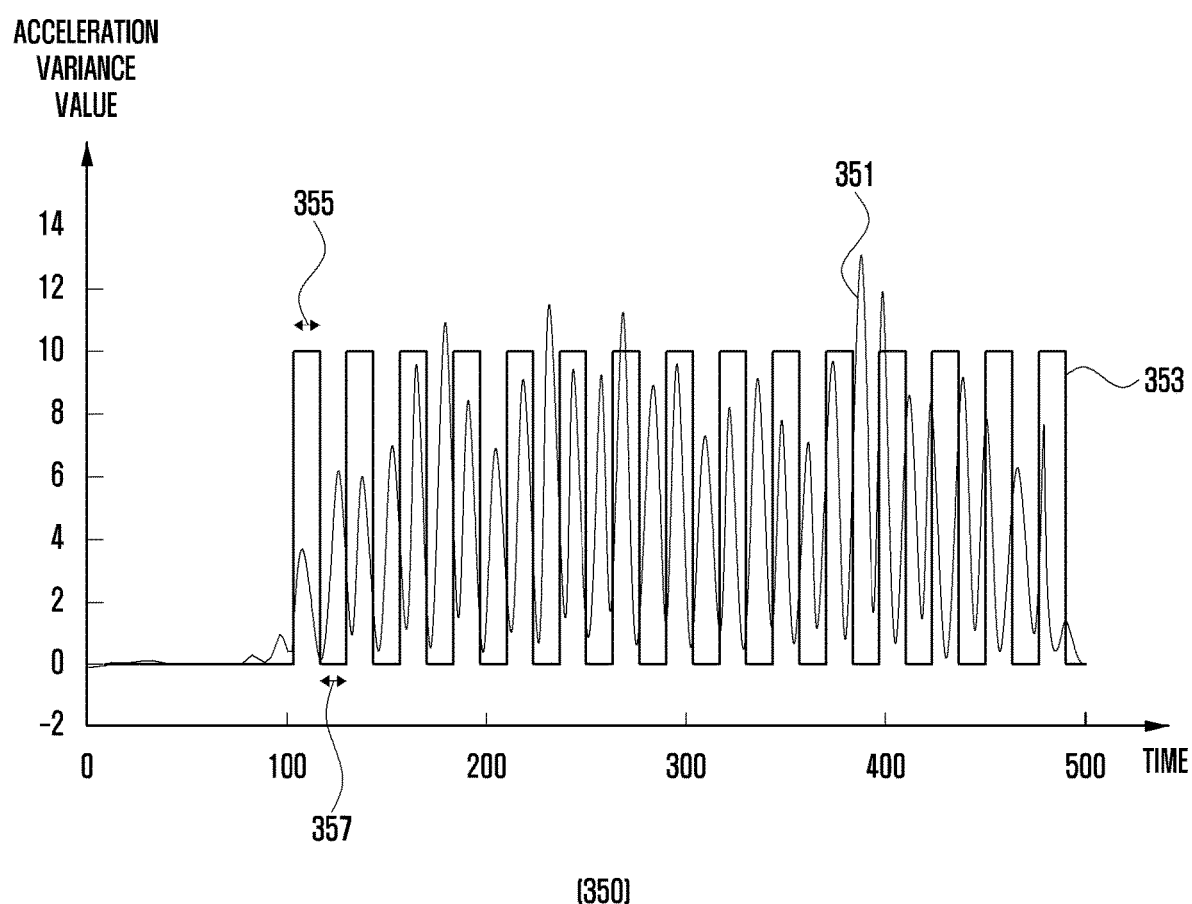

FIGS. 3A and 3B are diagrams illustrating an example of analyzing a walking pattern associated with the first operation mode according to an embodiment.

FIG. 3A is a first acceleration graph 310 associated with the walking pattern of the first operation mode.

Referring to FIG. 3A, a processor (for example, the processor 120) of an electronic device (for example, the electronic device 101 of FIG. 1) may obtain (or receive) an acceleration signal (or acceleration sensing signal) from an acceleration sensor (for example, the sensor module 176 of FIG. 1). The acceleration signal may include at least one of an x axis sensing signal 317, a y axis sensing signal 315, a z axis sensing signal 311, or a Ground Contact Time (GCT) signal 313. The acceleration signal shown in the first acceleration graph 310 may be a signal when the user having no difficulty in walking walks while wearing (or holding) the electronic device 101. In the x axis sensing signal 317, the y axis sensing signal 315, and the z axis sensing signal 311, signals (or acceleration value) varying according to the time may be symmetric and regular. The GCT signal 313 may be a signal indicating when the feet are touching the ground. In the GCT signal 313, a first section 318 in which the acceleration value is 10 may be the state in which the user's right foot touches the ground and a second section 319 in which the acceleration value is 0 may be the state in which the user's left foot touches the ground.

According to an embodiment, the processor 120 may determine symmetry (or symmetry level) on the basis of an interval ratio between the first section 318 and the second section 319 for a predetermined time. The symmetry may refer to left/right symmetry of the user body or left/right movement of the user body. The processor 120 may determine regularity (or regularity level) of the first section 318 and the second section 319 for a predetermined time. Regularity may refer to regularity of the walking pattern. The processor 120 may analyze the walking pattern of which an acceleration signal maintains a predetermined interval and is regular on the basis of the acceleration signal shown in the first acceleration graph 310. For example, when the acceleration signal shown in the first acceleration graph 310 is measured, the processor 120 may determine that symmetry and regularity exceed a reference value.

FIG. 3B illustrates a second acceleration graph 350 related to the walking pattern of the first operation mode.

Referring to FIG. 3B, a processor (for example, the processor 120) of an electronic device (for example, the electronic device 101 of FIG. 1) may calculate a variance signal 351 and a GCT signal 353 of the acceleration signal obtained from an acceleration sensor (for example, the sensor module 176 of FIG. 1). The variance signal 351 shown in the second acceleration graph 350 may be a signal which may appear when the user having no difficulty in walking walks while wearing (or holding) the electronic device 101. The processor 120 may determine undulation by using the variance signal 351 for a predetermined time. Undulation may indicate up/down symmetry of the user body or up/down movement of the user body. The processor 120 may determine undulation from the acceleration variance size indicated by the variance signal 351 for a predetermined time. In the second acceleration graph 350, it is noted that the acceleration variance size is substantially small and a regular pattern can be discerned.

When signals as shown in the first acceleration graph 310 and the second acceleration graph 350 are detected and patterns thereof are measured, the processor 120 may be configured to be in the first operation mode corresponding to the user having no difficulty in walking.

Figure 4A:
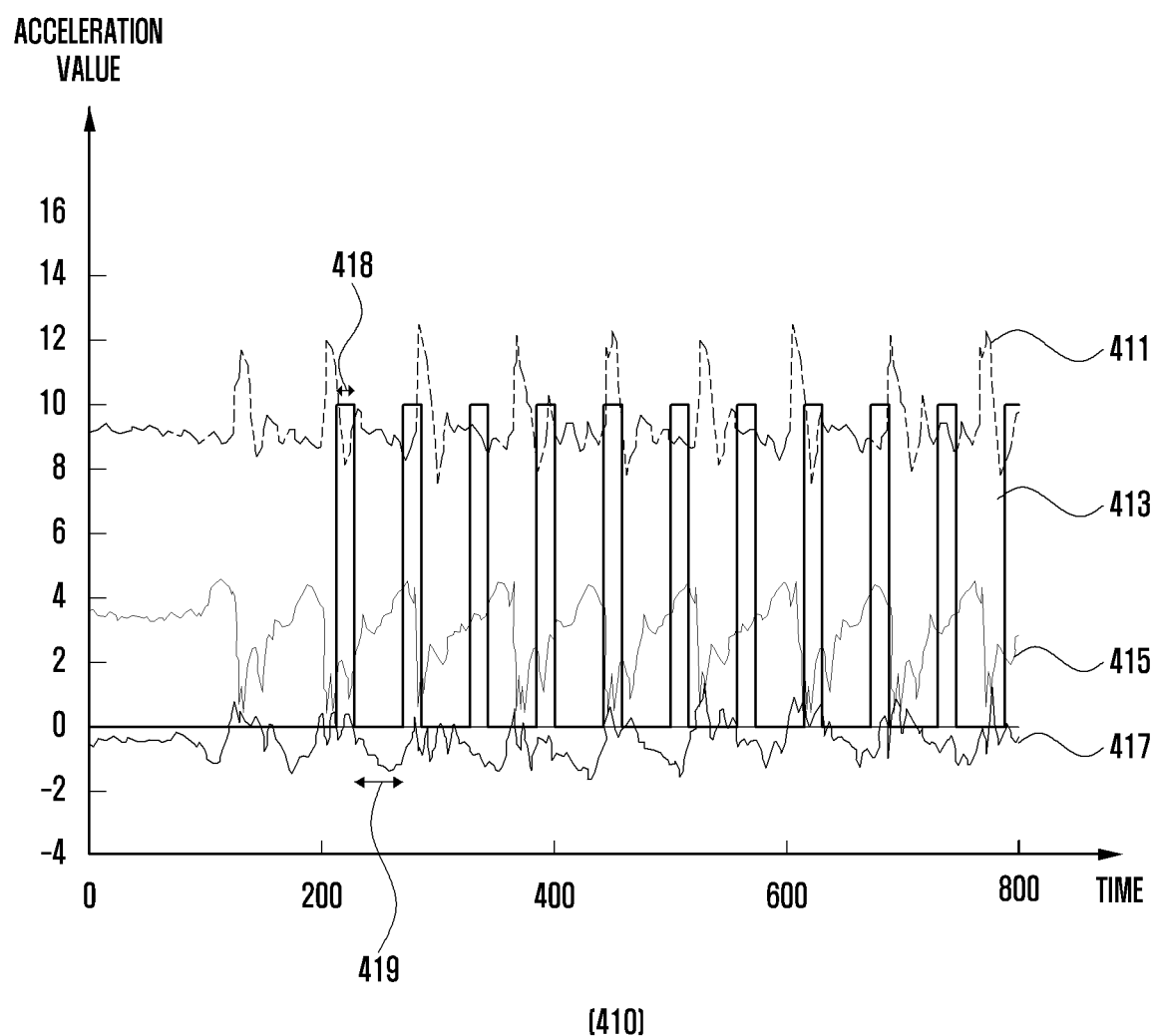
FIGS. 4A to 4C are diagrams illustrating examples of analyzing a walking pattern associated with the second operation mode according to an embodiment.
Figure 4B:
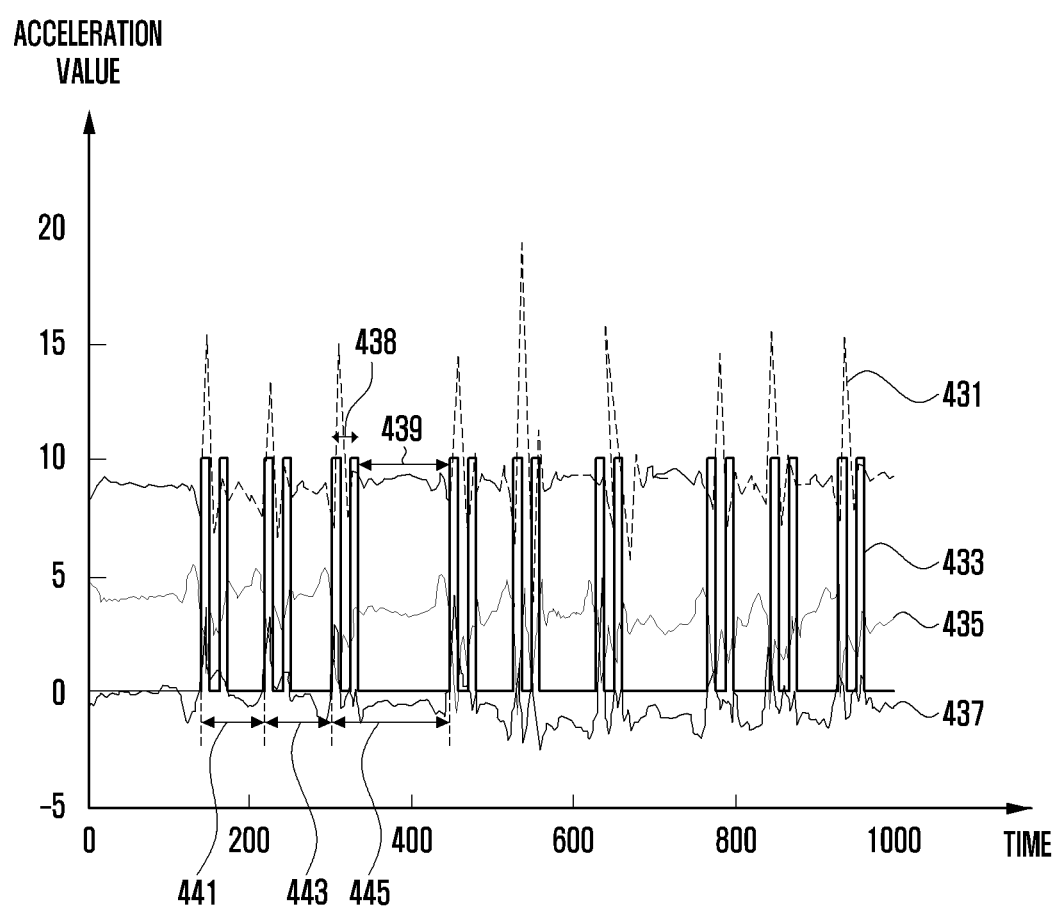
Figure 4C:
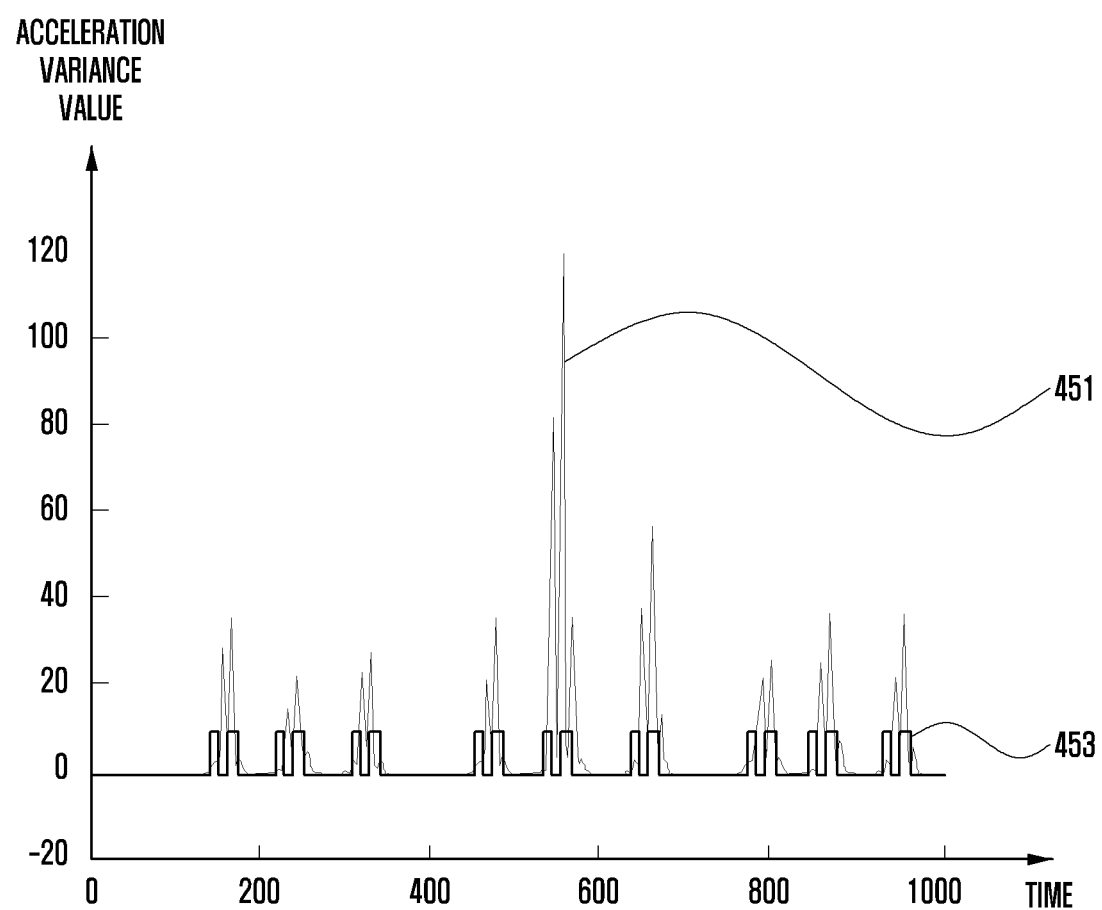

FIGS. 4A to 4C are diagrams illustrating examples of analyzing a walking pattern associated with the second operation mode according to an embodiment.

FIG. 4A is a third acceleration graph 410 associated with the walking pattern of the second operation mode.

Referring to FIG. 4A, a processor (for example, the processor 120) of an electronic device (for example, the electronic device 101 of FIG. 1) may obtain (or receive) an acceleration signal (or acceleration sensing signal) from an acceleration sensor (for example, the sensor module 176 of FIG. 1). The acceleration signal may include at least one of an x axis sensing signal 417, a y axis sensing signal 415, a z axis sensing signal 411, or a Ground Contact Time (GCT) signal 413. The acceleration signal shown in the third acceleration graph 410 may be a signal that may be detected when the user walks using an assist device (for example, crutches) while wearing (or holding) the electronic device. In the x axis sensing signal 417, the y axis sensing signal 415, and the z axis sensing signal 411, signals (or acceleration values) varying according to the time are symmetric and regular, but there is difference in symmetry and regularity compared to the x axis sensing signal 317, the y axis sensing signal 315, and the z axis sensing signal 311 of FIG. 3A.

In comparison between the acceleration signal of the first acceleration graph 310 and the acceleration signal of the third acceleration graph 410, there may be difference in the acceleration values. It is noted that the magnitude of acceleration of the z axis sensing signal 311 of the first acceleration graph 310 is low in a section in which the GCT signal 313 is 10 and is high in a section in which the GCT signal 313 is 0. On the other hand, it is noted that the magnitude of acceleration of the z axis sensing signal 411 of the third acceleration graph 410 is low in a section in which the GCT signal 413 is 10 and is high in a section in which the GCT signal 413 is changed from 0 to 10. This is because a subtle change in the magnitude of acceleration may be generated as a stepping axis of the crutches touches the ground along with the user feet. For example, the third acceleration graph 410 may be a signal that may be detected when the left side of the user (for example, the first section 418) is using crutches.

The GCT signal 413 may be a signal indicating that the user's feet are touching the ground. In the GCT signal 413, the first section 418 in which the acceleration value is 10 may be the state in which the user's right foot touches the ground and the second section 419 in which the acceleration value is 0 may be the state in which the user's left foot and the crutches touch the ground. In the GCT signal 413, the timing of the first section 418 and the second section 419 are not regular. In a comparison between the GCT signal 313 of the first acceleration graph 310 and the GCT signal 413 of the third acceleration graph 410 of FIG. 4A, there is difference in a section length. For example, while the stepping axis of the crutches touches the ground along with the user's left foot in the first section 418, only the user's right foot may touch the ground without any crutch in the second section 419. In a comparison between the timing (for example, timing of the second section 419) during which only the user's foot (for example, right foot) touches the ground and the timing (for example, timing of the first section 418) during which both the user's foot (for example, left foot) and the crutches touch the ground, the time interval during which only the right foot touches the ground is longer. The user walking with the crutches cannot walk with his/her own feet alone, and thus receive help from the crutches, and accordingly, the time during which the foot having no difficulty in walking may touch the ground for longer.

According to an embodiment, the processor 120 may determine symmetry (or symmetry level) on the basis of the interval ratio between the first section 418 and the second section 419 for a predetermined time and determine regularity of the first section 418 and the second section 419 for a predetermined time. In comparison between the third acceleration graph 410 and the first acceleration graph 310, the processor 120 may determine that symmetry or regularity is low. When the acceleration signal as shown in the third acceleration graph 410 is measured, the processor 120 may determine that symmetry and regularity are equal to or smaller than a reference value.

FIG. 4B illustrates a fourth acceleration graph 430 associated the walking pattern of the second operation mode.

Referring to FIG. 4B, a processor (for example, the processor 120) of an electronic device (for example, the electronic device 101 of FIG. 1) may obtain (or receive) an acceleration signal (or acceleration sensing signal) from an acceleration sensor (for example, the sensor module 176 of FIG. 1). The acceleration signal may include at least one of an x axis sensing signal 437, a y axis sensing signal 435, a z axis sensing signal 431, or a Ground Contact Time (GCT) signal 433. The acceleration signal as shown in the fourth acceleration graph 430 may be a signal that may be detected when the user walks using an assist device (for example, prosthetic leg) while wearing (or holding) the electronic device 101. In the x axis sensing signal 437, the y axis sensing signal 435, and the z axis sensing signal 431, signals (or acceleration values) varying according to time and are symmetric and regular, but there is difference in symmetry and regularity compared to the x axis sensing signal 317, the y axis sensing signal 315, and the z axis sensing signal 311 of FIG. 3A.

In a comparison between the acceleration signal of the first acceleration graph 310 of FIG. 3A and the acceleration signal of the fourth acceleration graph 430 of FIG. 4B, it is noted that there is difference in the acceleration value. It is noted that the magnitude of acceleration of the z axis sensing signal 311 of the first acceleration graph 310 is high in a section in which the GCT signal 313 is 0 and is low in a section in which the GCT signal 313 is 10. On the other hand, it is noted that the magnitude of acceleration of the z axis sensing signal 431 of the fourth acceleration graph 430 is high in a section in which the GCT signal 433 is 10 and is low in a section in which the GCT signal 433 is 0. The user walking with the prosthetic leg walks in short strides and the time during which the foot having no difficulty in walking is touching the ground may be longer.

The GCT signal 433 may be a signal indicating that the user's feet are touching the ground. In the GCT signal 433, the first section 438 in which the acceleration value is 10 may be the state in which the user's right foot is touching the ground and the second section 439 in which the acceleration value is 0 may be the state in which the user's prosthetic leg touches the ground. In the GCT signal 433, the timing of the first section 438 and the second section 439 are not regular. In a comparison between the GCT signal 313 of the first acceleration graph 310 and the GCT signal 433 of the fourth acceleration graph 430, it is noted that there is difference in the section length. For example, in the GCT signal 433, there are a first step 441, a second step 443, and a third step 445, and sections in which the accelerations of the first step 441 and the second step 443 are 0 are similar but a section in which the acceleration is 0 of the third step 445 is longer.

For example, while only the user's right foot touches the ground without any prosthetic leg in the first section 438, the user's left foot wearing the prosthetic touches the ground in the second section 439. In comparison between the timing during which only the user's foot (for example, right foot) touches the ground (for example, timing of the first section 438) and the timing during which the user's foot (for example, left foot) wearing the prosthetic leg touches the ground (for example, timing of the second section 439), it is noted that the time interval during which the prosthetic leg touches the ground is longer. When the user has a prosthetic left leg, immediately after moving the disabled leg (for example, left leg), the user moves the other side and transfers his or her center of gravity to the non-disabled leg (for example, right leg) to ambulate. The GCT signal 433 may have a pattern in which the first section 438 in which the acceleration value is 10 and the second section 439 in which the acceleration value is 0 each appear two times.

According to an embodiment, the processor 120 may determine symmetry (or symmetry level) on the basis of the interval ratio between the first section 438 and the second section 439 for a predetermined time and determine regularity of the first section 438 and the second section 439 for a predetermined time. In a comparison between the fourth acceleration graph 430 and the first acceleration graph 310, the processor 120 may determine that symmetry or regularity is low. When the acceleration signal as shown in the fourth acceleration graph 430 is measured, the processor 120 may determine that symmetry and regularity are equal to or smaller than a reference value.

Although the acceleration signals of the third acceleration graph 410 and the fourth acceleration graph 430 are different in the drawings, the acceleration signals may be similar even though assist devices are different. The drawings are only used for helping to understand the description, and do not limit the content of the disclosure.

FIG. 4C is a fifth acceleration graph 450 associated with the walking pattern of the second operation mode.

Referring to FIG. 4C, a processor (for example, the processor 120) of an electronic device (for example, the electronic device 101 of FIG. 1) may calculate a variance signal 451 and a GCT signal 453 of an acceleration signal obtained from an acceleration sensor (For example, the sensor module 176 of FIG. 1). The variance signal shown in the fifth acceleration graph 450 may be a signal that can be detected when the user wearing an assist device (for example, prosthetic leg) walks while wearing (or holding) the electronic device 101. The processor 120 may determine undulation by using the variance signal 451 for a predetermined time. Undulation may indicate up/down symmetry of the user body or up/down movement of the user body. The processor 120 may determine undulation from the acceleration variance size indicated by the variance signal 451 for a predetermined time. In the fifth acceleration graph 450, acceleration variance is substantially large and a pattern is regular, but is different from a walking pattern of the user having no difficulty in walking.

When the signal as shown in the third acceleration graph 410, the fourth acceleration graph 430, or the fifth acceleration graph 450 is detected and the pattern thereof is measured, the processor 120 may configure the second operation mode corresponding to the user walking by using the assist device.

According to an embodiment, in the case of the user walking while wearing a wearable robot, the acceleration signal shown in the third acceleration graph 410 or the fourth acceleration graph 430 may be detected. The processor 120 may determine the third operation mode on the basis of detection of the acceleration signal as shown in the third acceleration graph 410 or the fourth acceleration graph 430 and reception of device information from the wearable robot.

Figure 5A:
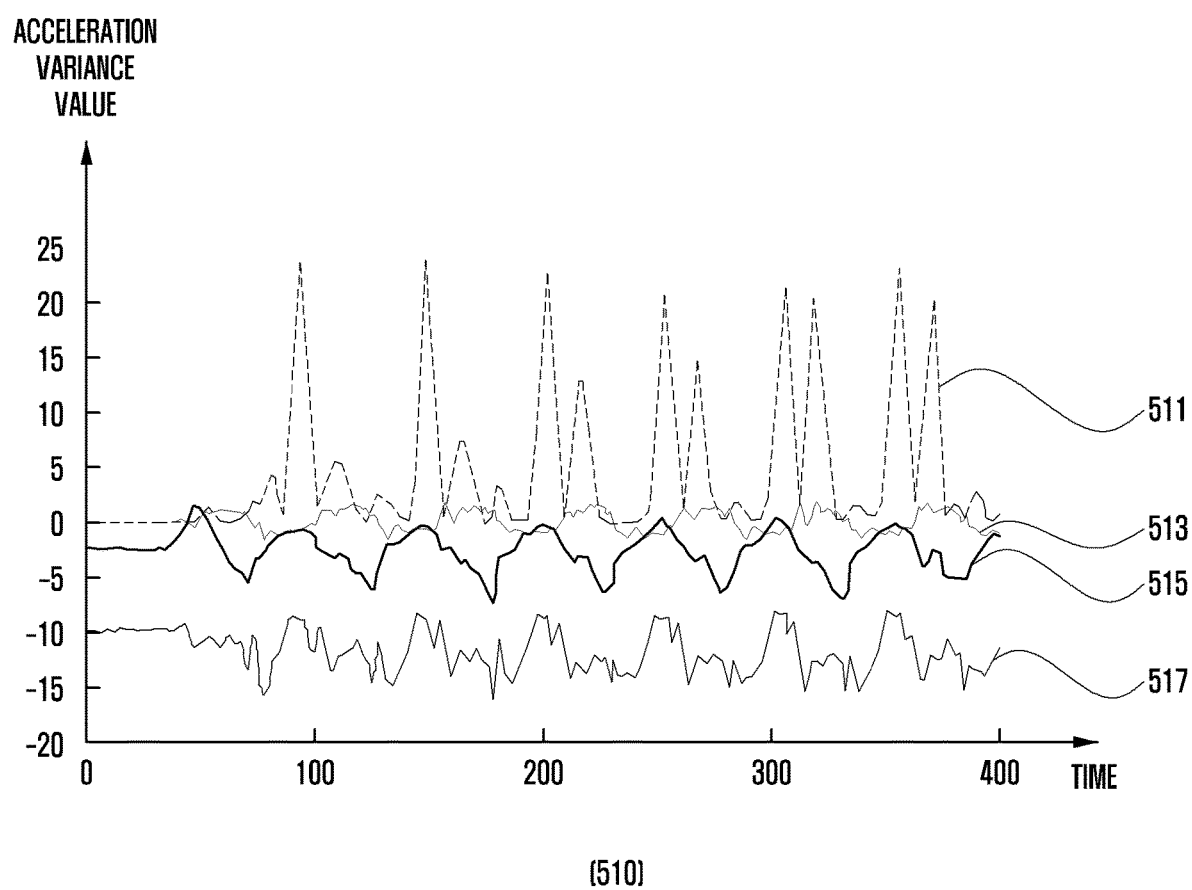
FIGS. 5A and 5B are diagrams illustrating examples of analyzing movement patterns associated with the first operation mode and the fourth operation mode according to an embodiment.
Figure 5B:
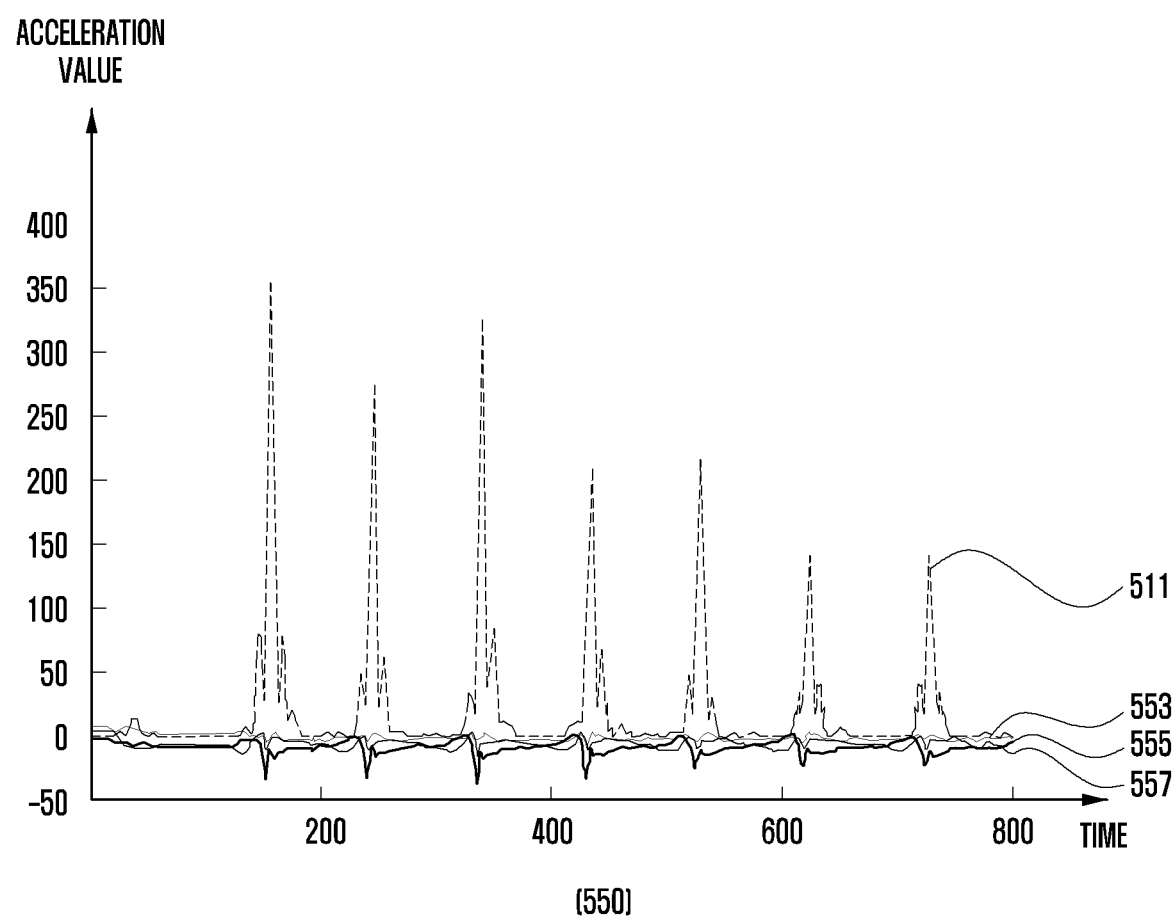

FIGS. 5A and 5B are diagrams illustrating examples of analyzing movement patterns associated with the first operation mode and the fourth operation mode according to an embodiment.

FIG. 5A is a sixth acceleration graph 510 illustrating an acceleration value measured in the first operation mode.

Referring to FIG. 5A, a processor (for example, the processor 120) of an electronic device (for example, the electronic device 101 of FIG. 1) may obtain (or measure) an acceleration signal from an acceleration sensor (for example, the sensor module 176 of FIG. 1). The acceleration signal may include at least one of an acceleration variance signal 511, an x axis sensing signal 517, a y axis sensing signal 515, or a z axis sensing signal 513. The sixth acceleration graph 510 may indicate an acceleration signal in the case in which the user having no difficulty in walking walks while wearing (or holding) the electronic device 101.

FIG. 5B is a seventh acceleration graph 550 illustrating an acceleration value measured in the second operation mode.

Referring to FIG. 5B, a processor (for example, the processor 120) of an electronic device (for example, the electronic device 101 of FIG. 1) may obtain (or measure) an acceleration signal from an acceleration sensor (for example, the sensor module 176 of FIG. 1). The acceleration signal may include at least one of an acceleration variance signal 551, an x axis sensing signal 557, a y axis sensing signal 555, or a z axis sensing signal 553. The seventh acceleration graph 550 indicate an acceleration signal in the case in which the user in the wheelchair moves while wearing (or holding) the electronic device 101.

It is noted that the acceleration value of the acceleration variance signal 551 of the seventh acceleration graph 550 is larger than that of the acceleration variance signal 511 of the sixth acceleration graph 510. Since the user having no difficulty in walking has a relatively free body (for example, hands), the acceleration variance value may not be large. The user in the wheelchair may have a larger acceleration variance because of a physical characteristic in which the user needs to push wheels to move the wheelchair. The physical characteristic may be force applied to wheels of the wheelchair. However, when the wheels of the wheelchair are slowly pushed, difference between an acceleration variance measured in the state in which the user is in the wheelchair and an acceleration variance of the user having no difficulty in walking may be small. In this case, the processor 120 may determine whether a movement characteristic of the user corresponds to the first operation mode or the fourth operation mode through the gyro sensor to further consider the movement trajectory of the hand.

Figure 6A:
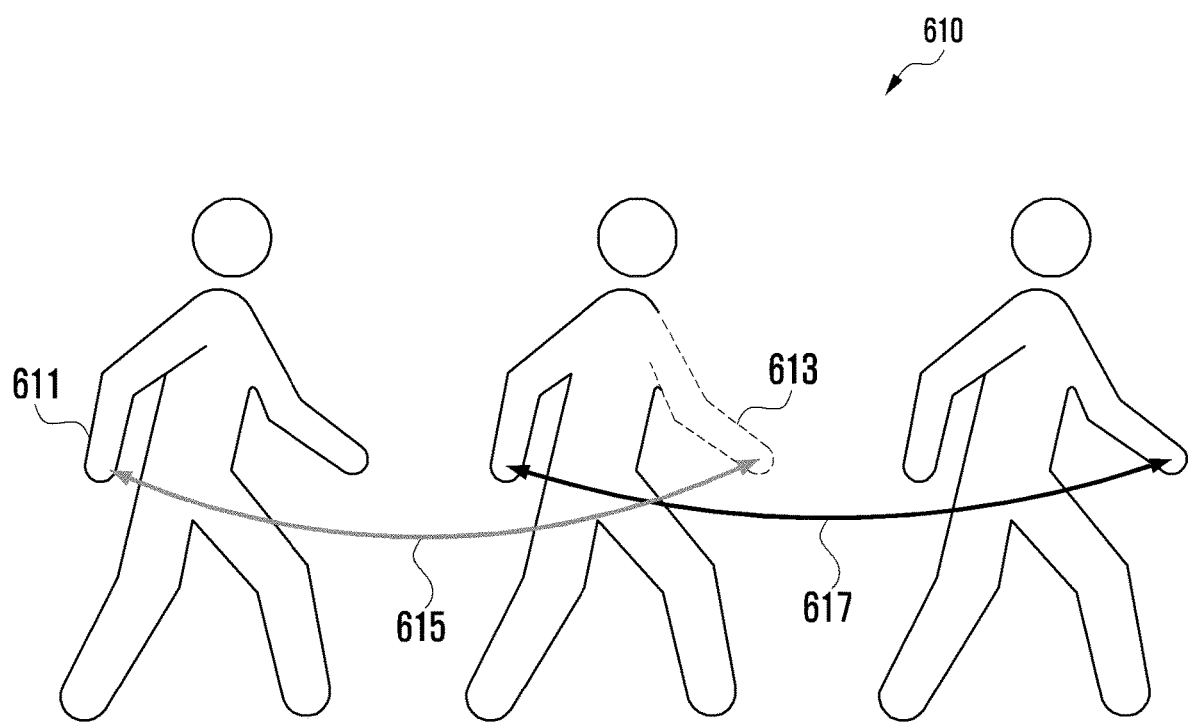
FIGS. 6A and 6B are diagrams illustrating movement trajectories associated with the first operation mode and the fourth operation mode according to an embodiment.
Figure 6B:
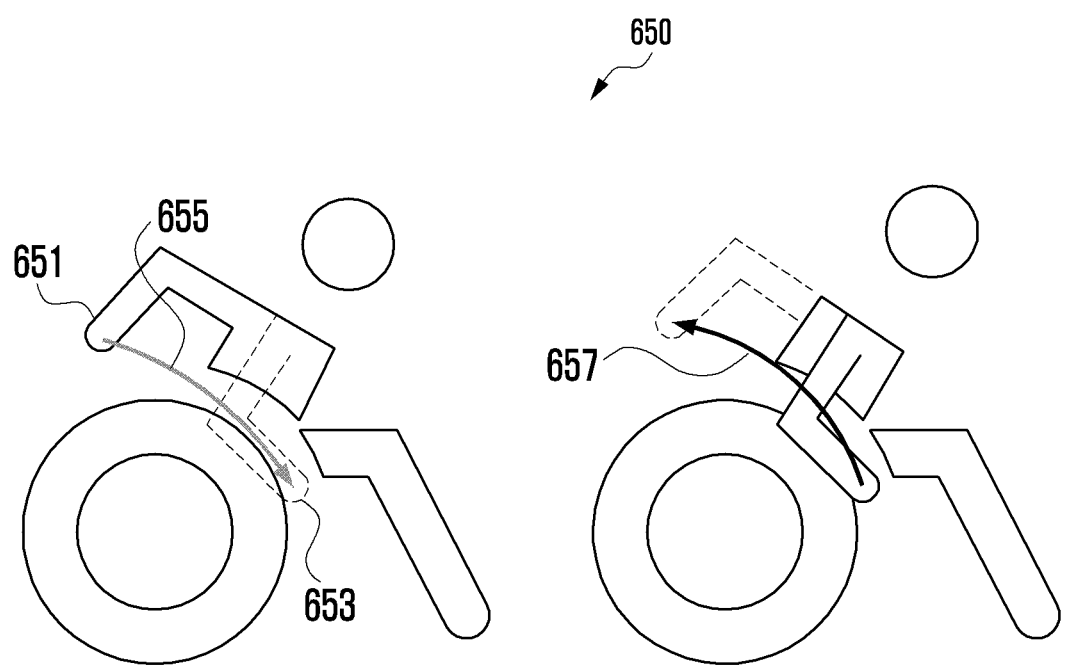

FIGS. 6A and 6B are diagrams illustrating movement trajectories associated with the first operation mode and the fourth operation mode according to an embodiment.

FIG. 6A illustrates a movement trajectory 610 on the basis of sensing data measured in the first operation mode.

Referring to FIG. 6A, a processor (for example, the processor 120) of an electronic device (for example, the electronic device 101 of FIG. 1) may obtain (or receive) an acceleration signal (or acceleration sensing signal) from an acceleration sensor (for example, the sensor module 176 of FIG. 1). The first operation mode may correspond to the user having no difficulty in walking. In the case of the user having no difficulty in walking, the movement trajectory is symmetric and regular. For example, a first movement trajectory 615 when the user having no difficulty in walking moves his/her right hand from the back (for example, a first position 611) to the front (for example, a second position 613) may be similar to (or the same as) a second movement trajectory 617 when the user moves his/her left hand from the back to the front. For example, when the user walks while wearing (for example, on the wrist) or holding (for example, with the hand) the electronic device 101, the user may walk swinging his/her hands back and forth.

At the first position 611, an acceleration value may be 10 and an angular speed value may not be detected. The angular speed value is a rotation value detected by a gyro sensor, and no angular speed value is detected since the user's hand is temporarily staying at the first position 611. When the user's hand moves from the first position 611 to the second position 613, an acceleration value larger than 0 may be detected and an angular speed value may be detected. As the user's hand moves from the first position 611 to the second position 613, an angular speed value may be detected along with an acceleration value. At the second position 613, an acceleration value may be 0 and an angular speed value may not be detected. Since the user's hand is temporarily staying at the second position 613, the angular speed value may not be detected. Referring to FIG. 3A to help understanding, the first position 611 may correspond to the second section 319 of the GCT signal 313 and the second position 613 may correspond to the first section 318 of the GCT signal 313 within the first acceleration graph 310.

According to an embodiment, the movement trajectory of the user receiving help in walking from an assist device (for example, crutches or prosthetic leg) may have left/right or up/down symmetry or an irregular characteristic. Referring to FIG. 4A to help understanding, the first position 611 may correspond to the second section 419 of the GCT signal 413 and the second position 613 may correspond to the first section 418 of the GCT signal 413 within the third acceleration graph 410.

FIG. 6B illustrates a movement trajectory 650 on the basis of sensing data measured in the fourth operation mode.

Referring to FIG. 6B, a processor (for example, the processor 120) of an electronic device (for example, the electronic device 101 of FIG. 1) may obtain (or receive) an acceleration signal (or acceleration sensing signal) from an acceleration sensor (for example, the sensor module 176 of FIG. 1). The fourth operation mode may correspond to a user in a wheelchair. In the fourth operation mode, a movement trajectory 650 occurs when the user is in a wheelchair—the movement of the user's hands rotating the wheels of the wheelchair may be detected as the movement trajectory. For example, a first movement trajectory 655 when the user in the wheelchair moves his/her hand (for example, right hand) from the back (for example, first position 651) to the front (for example, second position 653) may be different from a second movement trajectory 657 when the user moves his/her hand from the front (for example, second position 653) to the back (for example, first position 651). For example, when the user pushes the wheelchair while wearing (for example, on the wrist) or holding (for example, with the hand) the electronic device 101, the user holds and pushes wheels of the wheelchair with his/her hands when moving the hands from the back to the front, and thus the first movement trajectory 655 from the top to the bottom may be generated. Further, when the hand having moved forward moves backward, the second movement trajectory 657 from the bottom to the top may be generated. The movement trajectory 650 detected in the fourth operation mode may have left/right or up/down symmetry on the basis of comparison with the movement trajectory 610 detected in the first operation mode. The processor 120 may estimate (or predict) whether movement characteristic information is a walking pattern or a stroke pattern on the basis of the movement trajectory.

Figure 7:
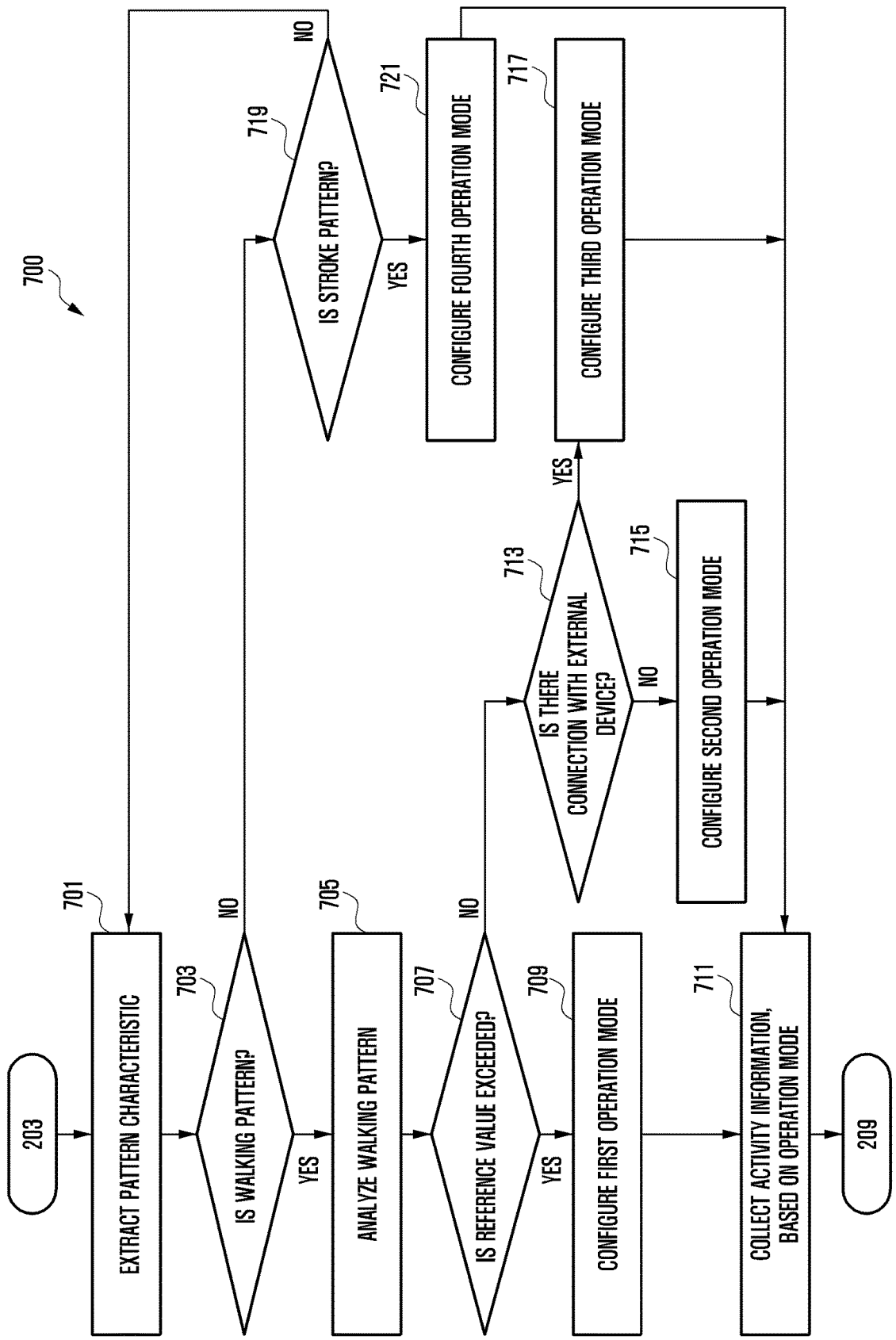
FIG. 7 is a flowchart 700 illustrating a method by which an electronic device analyzes a movement pattern characteristic and configuring an operation mode according to an embodiment.

FIG. 7 is a flowchart 700 illustrating a method by which an electronic device analyzes a movement pattern characteristic and configuring an operation mode according to an embodiment. The flowchart 700 of FIG. 7 indicates operation 205 and operation 207 of FIG. 2 in detail.

Referring to FIG. 7, in operation 701, a processor (for example, the processor 120) of an electronic device (for example, the electronic device 101 of FIG. 1) may extract a pattern characteristic. The processor 120 may extract a pattern characteristic from sensing data detected for a predetermined time (for example, 1 minute, 3 minutes, or 5 minutes). The pattern characteristic may indicate a periodic pattern or a consistent pattern that is not periodic.

In operation 703, the processor 120 may identify (or determine) whether the extracted pattern characteristic is a walking pattern. The walking pattern may correspond to the GCT signal (for example, the GCT signal 313, the GCT signal 413, or the GCT signal 433) of the acceleration graph as illustrated in FIG. 3A, 4A, or 4B (for example, the first acceleration graph 310, the third acceleration graph 410, the fourth acceleration graph 430). For example, the processor 120 may identify whether a GCT signal of which the acceleration value of 0 or 10 is periodically changed at regular time intervals (for example, 1 second, 2 seconds, or 3 seconds). When the GCT signal is extracted (or measured) from the acceleration sensor value, the processor 120 may determine the walking pattern. Alternatively, the walking pattern may be indicated by a consistent pattern between x, y, and z signals of the acceleration signal. For example, when acceleration values of an x axis acceleration signal (for example, the x axis signal 317 of FIG. 3A) and a y axis acceleration signal (for example, the y axis signal 315 of FIG. 3A) are high at regular time intervals when an acceleration value of an z axis acceleration signal (for example, the z axis signal 311 of FIG. 3A) is low, the processor 120 may determine walking pattern. When the GCT signal is detected and a consistent pattern between the x, y, and z signals of the acceleration signal is detected, the processor 120 may determine the walking pattern.

The processor 120 may perform operation 705 when the walking pattern is detected from the extracted pattern characteristic and perform operation 719 when the walking pattern is not detected from the extracted pattern characteristic. Although it is illustrated that operation 703 is first performed and then operation 719 is performed in the drawings, operation 719 may be first performed and then operation 703 may be performed or operation 703 and operation 719 may be concurrently performed. This is only an issue in implementation of the electronic device 101 and does not limit the content of the disclosure.

When the walking pattern is detected, the processor 120 may analyze the walking pattern in operation 705. The processor 120 may analyze the walking pattern on the basis of at least one of the GCT signal, the x, y, and z values of the acceleration signal, or the acceleration variance value. The processor 120 may identify (or determine) at least one of symmetry, regularity, and undulation on the basis of at least one of the GCT signal, the x, y, and z values of the acceleration signal, or the acceleration variance value. For example, the processor 120 may determine symmetry on the basis of an interval ratio between the first section (for example, the first section 318, the first section 418, or the first section 438) and the second section (for example, the second section 319, the second section 419, or the second section 439) of the GCT signal (for example, the GCT signal 313, the GCT signal 413, or the GCT signal 433). The symmetry may indicate left/right symmetry of the user body or left/right movement of the user body.

The processor 120 may determine the first section and the second section of the GCT signal for a predetermined time. Regularity may refer to regularity of a walking pattern. The processor 120 may determine undulation on the basis of the acceleration variance value measured (or obtained) for a predetermined time. Undulation may indicate up/down symmetry of the user body or up/down movement of the user body.

In operation 707, the processor 120 may identify (or determine) the mode on the basis of the analysis result. For example, when at least one of the symmetry, the regularity, and the undulation exceeds a reference value, the processor 120 may identify the first operation mode. When the time intervals of the first section and the second section of the GCT signal are the same as each other, the processor 120 may determine that symmetry exceeds a reference value. When the first section and the second section are regular in the GCT signal, the processor 120 may determine that regularity exceeds a reference value. When the acceleration variance value measured (or obtained) for a predetermined time is detected in accordance with the GCT signal, the processor 120 may determine that the undulation exceeds a reference value. For example, when a maximum value and a minimum value of the variance value are within a predetermined value from a maximum value and a minimum value of the GCT signal, the processor 120 may determine that the undulation exceeds a reference value.

According to an embodiment, when at least one of the symmetry, the regularity, and the undulation does not exceed the reference value, the processor 120 may identify the second operation mode or the third operation mode. When the time of the first section and the time of the second section of the GCT signal are not the same (for example, FIG. 4A or FIG. 4B), the processor 120 may determine that the symmetry is equal to or smaller than the reference value. When the first section and the second section are not regular in the GCT signal (for example, FIG. 4A or FIG. 4B), the processor 120 may determine that the regularity is equal to or smaller than the reference value. When the acceleration variance value measured (or obtained) for a predetermined time is not detected in accordance with the GCT signal, the processor 120 may determine that the undulation is equal to or smaller than the reference value. For example, when difference between a maximum value and a minimum value of the variance value and a maximum value and a minimum value of the GCT signal exceeds a predetermined value, the processor 120 may determine that the undulation is equal to or smaller than the reference value.

The processor 120 may perform operation 709 or operation 713 on the basis of the analysis result.

When the reference value is exceeded, the processor 120 may configure the electronic device 101 to be in the first operation mode in operation 709. The first operation mode may correspond to a user having no difficulty in walking. The user having no difficulty in walking is a typical user and may mean that there is no difficulty in walking or running, so that the user does not require an assist device. After performing operation 709, the processor 120 may perform operation 711.

When the reference value is not exceeded, the processor 120 may identify (or determine) whether there is a connection with an external device corresponding to an assist device in operation 713. The external device is a device helping the user in walking and may be a device such as a wearable smart device such as a wearable exoskeleton. The processor 120 may obtain device information of the external device from the user in advance or receive the device information from the external device so as to make the connection with the external device. The processor 120 may perform operation 715 or operation 717 on the basis of information indicating that the walking pattern is detected but the symmetry, the regularity, and the undulation are equal to or smaller than the reference value and whether the connection with the external device is made. The processor 120 may perform operation 715 when the connection with the external device is not made, and perform operation 717 when the connection with the external device is made.

When the connection with the external device is not made, the processor 120 may configure the electronic device 101 to be in the second operation mode in operation 715. The second operation mode may correspond to the user using an assist device such as crutches or prosthetic legs). The assist device worn or used by the user corresponding to the second operation mode may not include a communication module (for example, wireless communication module). After performing operation 715, the processor 120 may perform operation 711.

When the connection with the external device is made, the processor 120 may configure the electronic device 101 to be in the third operation mode in operation 717. The third operation mode may correspond to the user using an assist device such as a wearable exoskeleton. The assist device worn or used by the user corresponding to the third operation mode may include a communication module. After performing operation 717, the processor 120 may perform operation 711.

When the walking pattern is not detected, the processor 120 may identify (or determine) whether the extracted pattern characteristic is a stroke pattern in operation 719. The stroke pattern may be measured by movement trajectory when the user is in a wheelchair—the movement of the user's hands to rotate the wheels of the wheelchair may be detected as the movement trajectory. In the stroke pattern, the movement trajectory (for example, the first movement trajectory 655 of FIG. 6B) when the user's hands move from the back to the front may be different from the movement trajectory (for example, the second movement trajectory 657 of FIG. 6B) when the user's hands move from the front to the back. In the case of the stroke pattern, when the user moves his/her hand from the back to the front, the user pushes wheels of the wheelchair with his/her hands, and thus a movement trajectory from the top to the bottom may be generated. Further, when the hand having moved to the front is moved to the back, a movement trajectory from the bottom to the top may be generated.

The processor 120 may perform operation 721 when the extracted pattern characteristic is the stroke pattern, and return to operation 701 when the extracted pattern characteristic is not the stroke pattern. When the processor 120 returns to operation 701, the processor may perform operation 701 again for a predetermined time (for example, 1 minute or 3 minutes) and then perform operation 703 or operation 719 if the corresponding pattern (e.g. walking pattern) is detected.

When the extracted pattern characteristic is the stroke pattern, the processor 120 may configure the electronic device 101 to be in the fourth operation mode in operation 721. The fourth operation mode may correspond to the user being in (or using) a wheelchair. When the movement feature information corresponds to the stroke pattern, the processor 120 may identify the fourth operation mode in accordance with the user using the electronic device 101. After performing operation 721, the processor 120 may perform operation 711.

In operation 711, the processor 120 may collect activity information on the basis of the operation mode. The processor 120 may collect activity information in different schemes according to the operation mode configured in the electronic device 101 and may differentiate between the collected activity information. The activity information may include at least one of the number of steps, healthy walking, the number of strokes, running, calories (burned calories), activity time, the number of floors climbed or descended, or the ascended height. When the electronic device 101 is configured to be in the first operation mode, the processor 120 may collect activity information on the basis of the first operation mode. The activity information based on the first operation mode may include at least one of the calories, the activity time, the number of steps, the running, the healthy walking (or the number of healthy steps), or the number of floors climbed or descended.

According to an embodiment, the processor 120 may reduce power consumption due to the control (or performance) of a function engine by controlling the function engine for collecting (or analyzing) the activity information according to the operation mode. In the first operation mode, the processor 120 may not calculate some pieces of the activity information (for example, the number of strokes or the ascended height) according to the user body condition.

According to an embodiment, when the electronic device 101 is configured to be in the second operation mode, the processor 120 may collect activity information on the basis of the second operation mode. The activity information based on the second operation mode may include at least one of the calories, the activity time, the number of steps, or the number of floors climbed or descended. In the second operation mode, the processor 120 may not calculate some pieces of activity information (for example, healthy walking, running, the number of strokes, or the ascended height) according to the condition of the user's body.

According to an embodiment, when the electronic device 101 is configured to be in the third operation mode, the processor 120 may collect activity information on the basis of the third operation mode. The activity mode based on the third operation mode may include at least one of the calories, the activity time, the number of steps, or the number of floors climbed or descended. The activity information based on the third operation mode may be the same as or different form the activity information based on the second operation mode. The processor 120 may receive device information through the communication module (for example, the communication module 190 of FIG. 1) from the assist device and collect activity information related to the third operation mode on the basis of the received device information. In the third operation mode, the processor 120 may not calculate some pieces of activity information (for example, healthy walking, running, the number of strokes, or the ascended height) according to the user body condition.

According to an embodiment, when the electronic device 101 is configured to be in the fourth operation mode, the processor 120 may collect activity information on the basis of the fourth operation mode. The activity information based on the fourth operation mode may include at least one of the calories, the activity time, the number of strokes, or the ascended height. The processor 120 may measure (or calculate) the number of strokes or the ascended height instead of measuring the number of steps, the healthy walking, and the number of floors climbed or descended. The processor 120 may not calculate some pieces of activity information (for example, the number of steps, the healthy walking, the running, and the number of floors climbed or descended) according to the user body condition.

Figure 8:
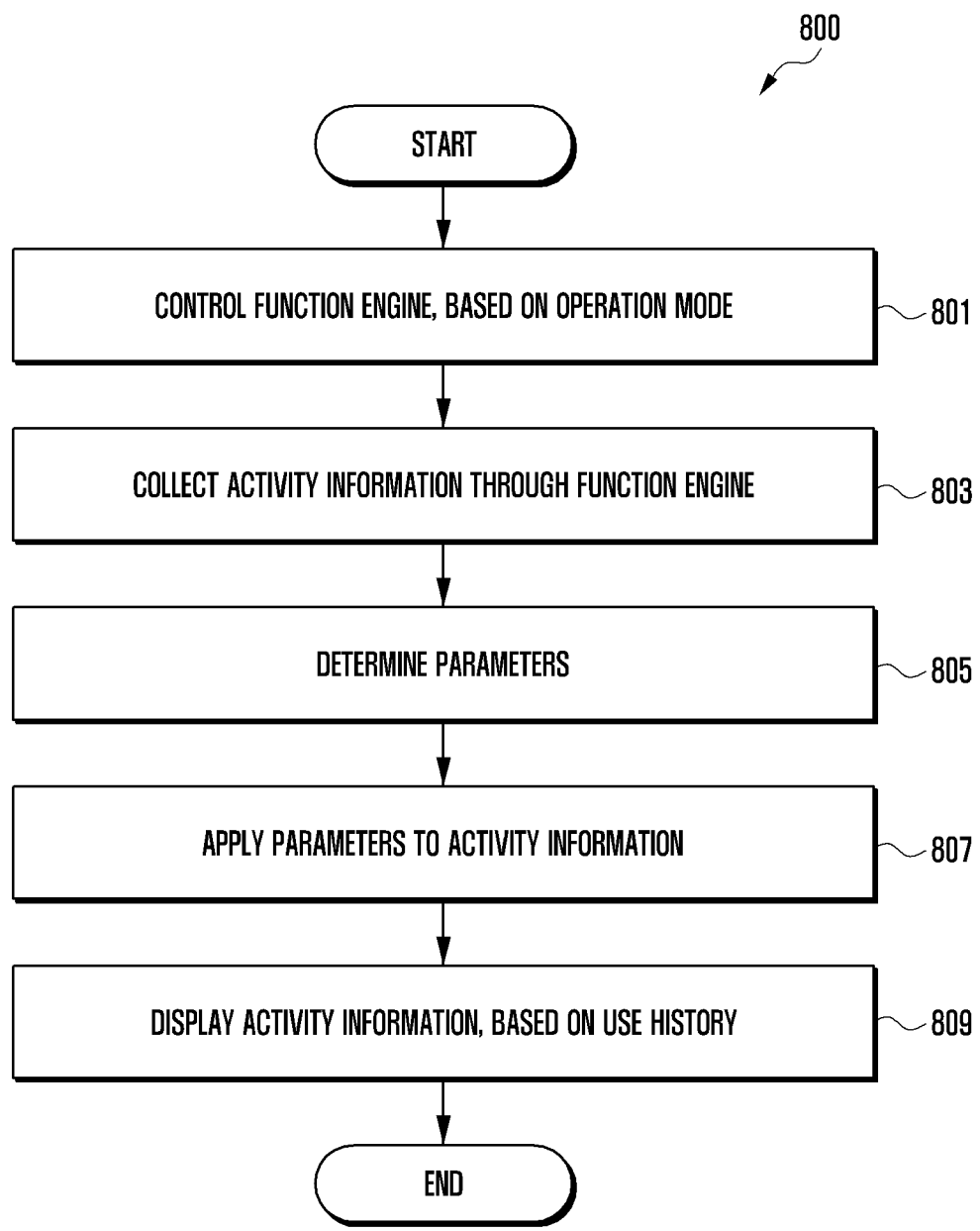
FIG. 8 is a flowchart 800 illustrating a method by which an electronic device collects and provides activity information according to an embodiment.

FIG. 8 is a flowchart 800 illustrating a method by which an electronic device collects and provides activity information according to an embodiment.

Referring to FIG. 8, in operation 801, a processor (for example, the processor 120) of an electronic device (for example, the electronic device 101 of FIG. 1) may control a function engine on the basis of an operation mode. The function engine may be a program (or software) used to collect or analyze the activity information. The operation mode may be one of a first operation mode to a fourth operation mode. The processor 120 may reduce power consumption according to the control (or performance) of the function engine by controlling the function engine for collecting (or analyzing) activity information according to the operation mode configured in the electronic device 101.

For example, when the electronic device 101 is in the first operation mode, the processor 120 may turn off (or deactivate) the function engine for measuring (or calculating) the number of strokes or the ascended height. In the first operation mode, the processor 120 may turn on (or activate) the function engine for measuring (or calculating) at least one of the calories, the activity time, the number of steps, the healthy walking, or the number of floors climbed or descended. When the electronic device 101 is in the second operation mode, the processor 120 may activate the function engine for measuring at least one of the calories, the activity time, the number of steps, or the number of floors climbed or descended and deactivate the function engine for measuring at least one of the healthy walking, the running, the number of strokes, or the ascended height.

When the electronic device 101 is in the third operation mode, the processor 120 may activate the function engine for measuring at least one of the calories, the activity time, the number of steps, or the number of floors climbed or descended and turn off the function engine for measuring at least one of the healthy walking, the running, the number of strokes, or the ascended height. In the fourth operation mode, the processor 120 may activate the function engine for measuring at least one of the calories, the activity time, the number of strokes, or the ascended height and deactivate the function engine for measuring at least one of the number of steps, the healthy walking, the running, the number of floors climbed or descended.

In operation 803, the processor 120 may collect activity information by using the function engine. For example, the processor 120 may collect the activity information by using the activated function engine while other function engines are deactivated by operation 801. In the first operation mode, the processor 120 may collect activity information corresponding to the first operation mode by using the function engine for measuring (or calculating) at least one of the calories, the activity time, the number of steps, the running, the healthy walking, or the number of floors climbed or descended. In the second operation mode, the processor 120 may collect activity information corresponding to the second operation mode by using the function engine for measuring at least one of the calories, the activity time, the number of steps, or the number of floors climbed or descended. In the third operation mode, the processor 120 may collect activity information corresponding to the third operation mode by using the function engine for measuring at least one of the calories, the activity time, the number of steps, or the number of floors climbed or descended. In the fourth operation mode, the processor 120 may collect activity information corresponding to the fourth operation mode by using the function engine for measuring at least one of the calories, the activity time, the number of strokes, or the ascended height.

In operation 805, the processor 120 may determine parameters. The processor 120 may determine different parameters according to the operation mode. The parameters may be applying different weight values to information included in activity information corresponding to the respective operation modes. For example, the processor 120 may determine a first parameter for the first operation mode, a second parameter for the second operation mode, a third parameter for the third operation mode, and a fourth parameter for the fourth operation mode on the basis of the use history. The first parameter to the fourth parameter may be the same as or different from each other.

In operation 807, the processor 120 may apply the determined parameter to the collected activity information. For example, the first parameter may be applying a weight value different from weight values of the second parameter to the fourth parameter to at least one of the calories, the activity time, the number of steps, the running, the healthy walking, or the number of floors climbed or descended. For example, the first parameter may have a weight value larger than a weight value of the second parameter or the third parameter with respect to the calories, the activity time, the number of steps, or the number of floors climbed or descended. Alternatively, on the other hand, the first parameter may have a weight value smaller than a weight value of the second parameter or the third parameter. Accordingly, although the same number of steps is measured in the first operation mode, the second operation mode, and the third operation mode, calories or activity time may be different. Alternatively, the fourth parameter may have a weight value smaller than weight values of the first parameter to the third parameter. This is only a description for helping understanding of the disclosure and does not limit the content of the disclosure.

According to an embodiment, the processor 120 may reevaluate the parameters on the basis of at least one of a movement condition of the user of the electronic device 101 or the collected activity information. The processor 120 may provide more accurate activity information by periodically or selectively controlling the parameters applied to the activity information.

In operation 809, the processor 120 may display the activity information on a display (for example, the display device 160 of FIG. 1) on the basis of the use history. The use history may include at least one of a time during which the user uses the electronic device 101, an application (or function), information on a location at which the electronic device 101 is used, or configuration information of the electronic device 101. Even though the same operation mode is configured in the electronic device 101, the processor 120 may display different pieces of activity information for users on the basis of the use history. For example, when the electronic device 101 is configured to be in the first operation mode, the processor 120 may display at least one of the calories, the activity time, or the number of steps for a first user on the basis of the use history of the first user, and display at least one of the number of steps, the number of healthy steps, or the activity time for a second user on the basis of the use history of the second user.

According to an embodiment, since pieces of information that different users mainly use or need may be different, the processor 120 may recommend useful activity information to the user or perform control to automatically display useful activity information when learning the use history and switching the operation mode.

FIG. 9 is a diagram illustrating an example of a user interface for displaying activity information in an electronic device according to an embodiment.

Referring to FIG. 9, a processor (for example, the processor 120 of FIG. 1) of an electronic device (for example, the electronic device 101 of FIG. 1) may display a user interface including first activity information 910 on a display (for example, the display device 160 of FIG. 1). The first activity information 910 may include at least one of calories 911, exercise time 913, or activity time 957. The first activity information 910 may be displayed in a heart shape including the calories 911, the exercise time 913, or the activity time 957. Hereinafter, the heart shape for displaying the activity information is only an example, and the activity information may be displayed in various shapes such as a triangle, a rectangle, a circle, an oval, a semicircle, a triangular pyramid, a cone, a polygon, and the like. The processor 120 may display the activity information (for example, the calories 911, the exercise time 913, and the activity time 957) in different colors. When each piece of the activity information configured by the user or the electronic device 101 in advance reaches a target value, the processor 120 may display a complete heart shape for the activity information, and when the activity information does not reach the target value, may not display the complete heart shape. For example, the processor 120 may display activity information that reaches the target value in a darker color than activity information that does not reach the target value.

The processor 120 may display a user interface including the second activity information 930 on the display device 160. The processor 120 may display the second activity information 930 on the basis of a user's scroll input (for example, a touch input from the bottom to the top on the screen (for example, vertical drag)) in the state in which the first activity information 910 is displayed. The second activity information 930 may include image activity information 931 and text activity information 933. The image activity information 931 may be displayed in a heart shape and may indicate how much the activity information (for example, the calories 911, the exercise time 913, and the activity time 957) has reached the target value. For example, the image activity information 931 may indicate that the calories 911 reach 14% of the target value, the exercise time 913 reaches 0% of the target value, and the activity time 957 reaches 25% of the target value. The text activity information 933 may indicate a satisfied activity (for example, 14 Cal) and a target value (for example, 300 Cal) in text.

The processor 120 may display a user interface including the third activity information 950 on the display device 160. The processor 120 may display the third activity information 950 on the basis of a user's scroll input in the state in which the second activity information 930 is displayed. The third activity information 950 may indicate satisfaction values (for example, 14 Cal, 0 Mins, and 2 hrs) and target values (for example, 300 Cal, 30 Mins, and 8 hrs) for the calories 951, the exerciser 953, and the activity time 957 in text.

The processor 120 may display a user interface including the fourth activity information 970 on the display device 160. The processor 120 may display the fourth activity information 970 on the basis of a user's scroll input (for example, a touch input (for example, horizontal drag) moving from the left side (or right side) to the right side (or left side) on the screen) in the state in which the first activity information 910 to the third activity information 950 are displayed. The fourth activity information 970 may include daily activity information 971 and a setting button 973. The daily activity information 971 may indicate activity information per day with respect to activity information collected for one week. The user may review activity information for one week at a glance through the daily activity information 971. The setting button 973 may be to change settings related to activity information such as changing information to be displayed as activity information or changing a shape of the activity information. When the user selects the setting button 973, the processor 120 may provide a user interface for various settings such as settings to change information or user interface shape.

According to an embodiment, the first activity information 910 to the fourth activity information 970 may be displayed in the electronic device 101 configured to be one operation mode (for example, the first operation mode) among the first operation mode to the fourth operation mode.

Figure 10:
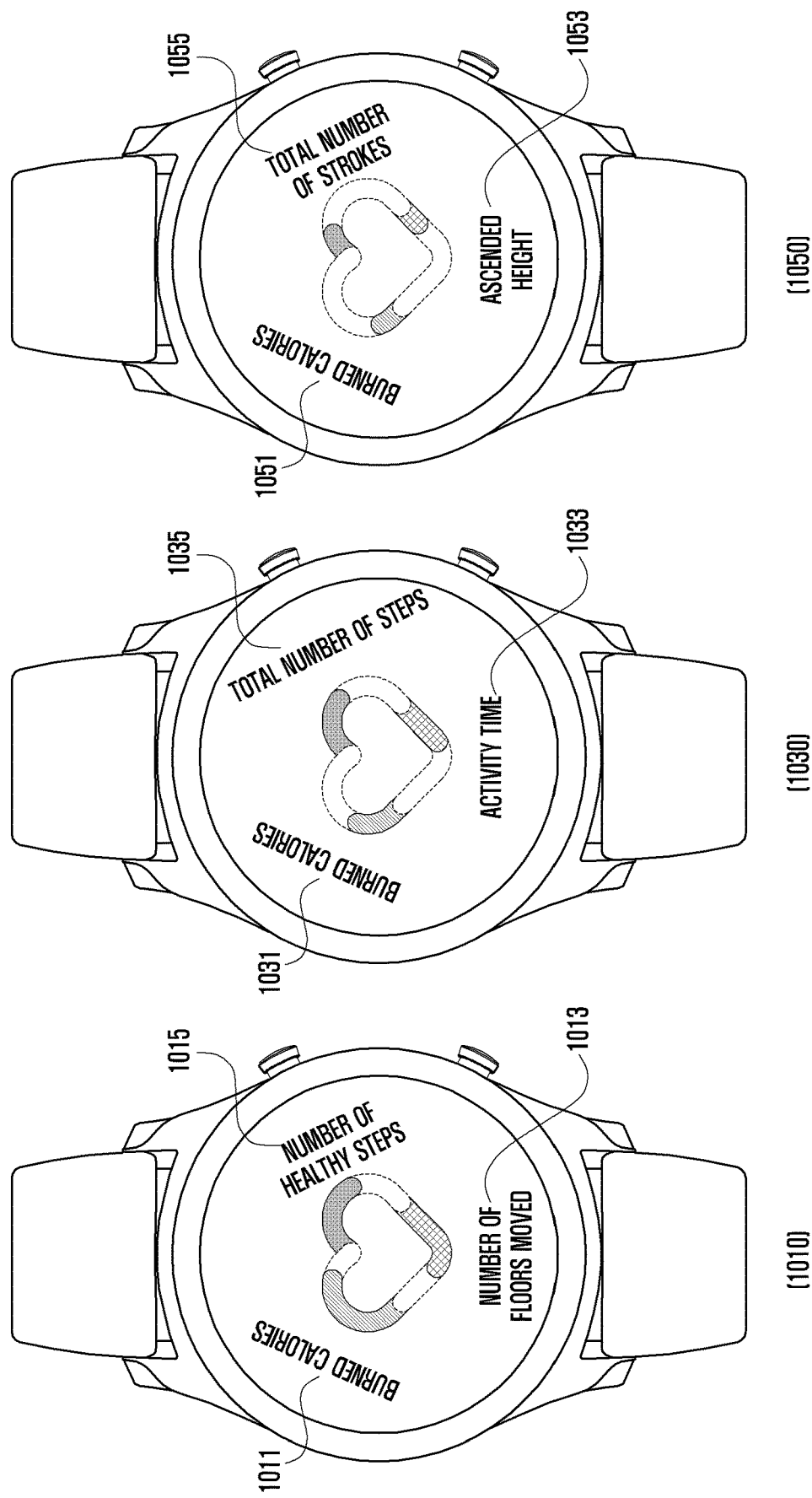
FIGS. 10 to 12 are diagrams illustrating examples in which an electronic device displays activity information according to an operation mode according to various different embodiments.
Figure 11:
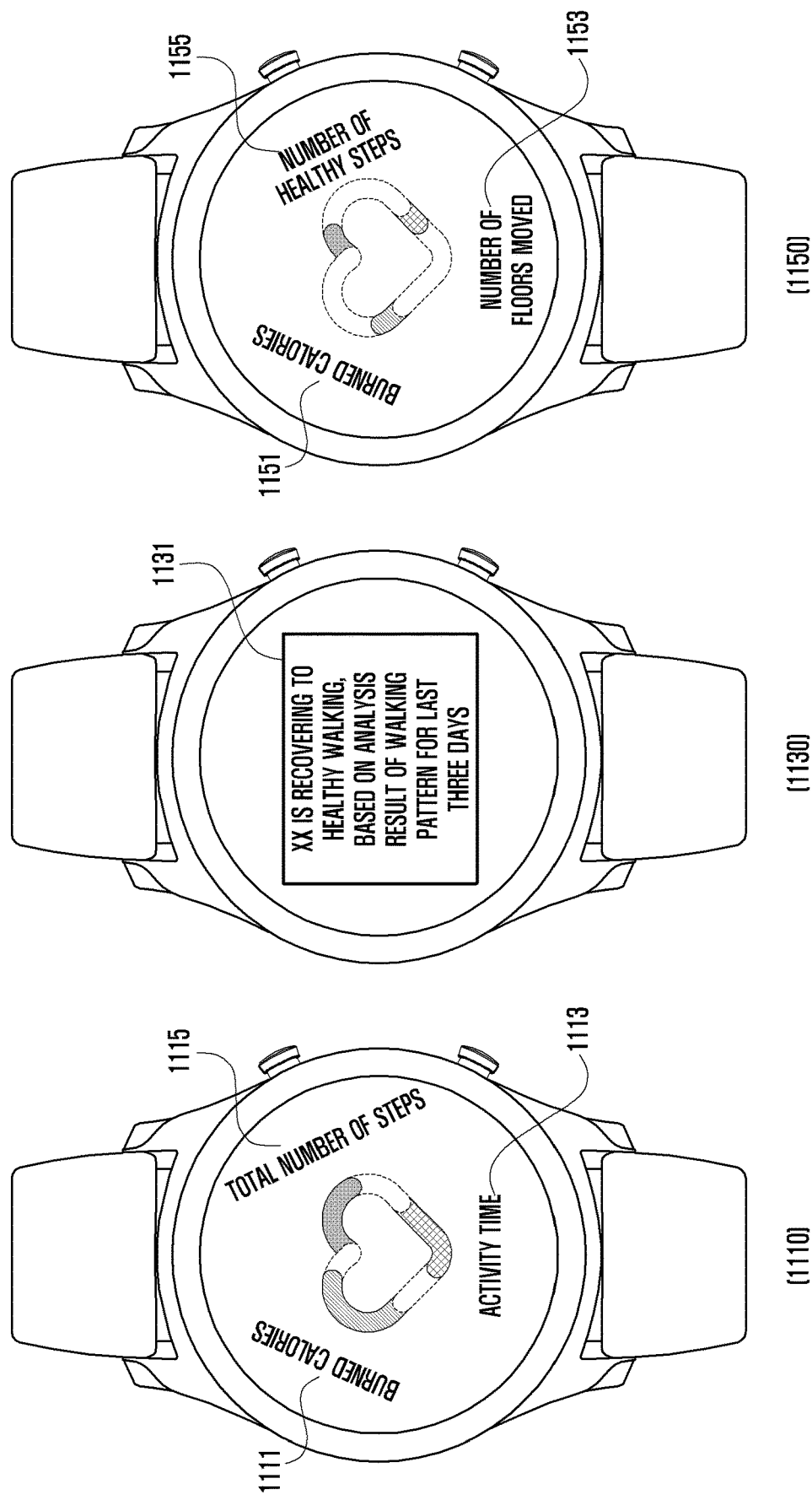
Figure 12:
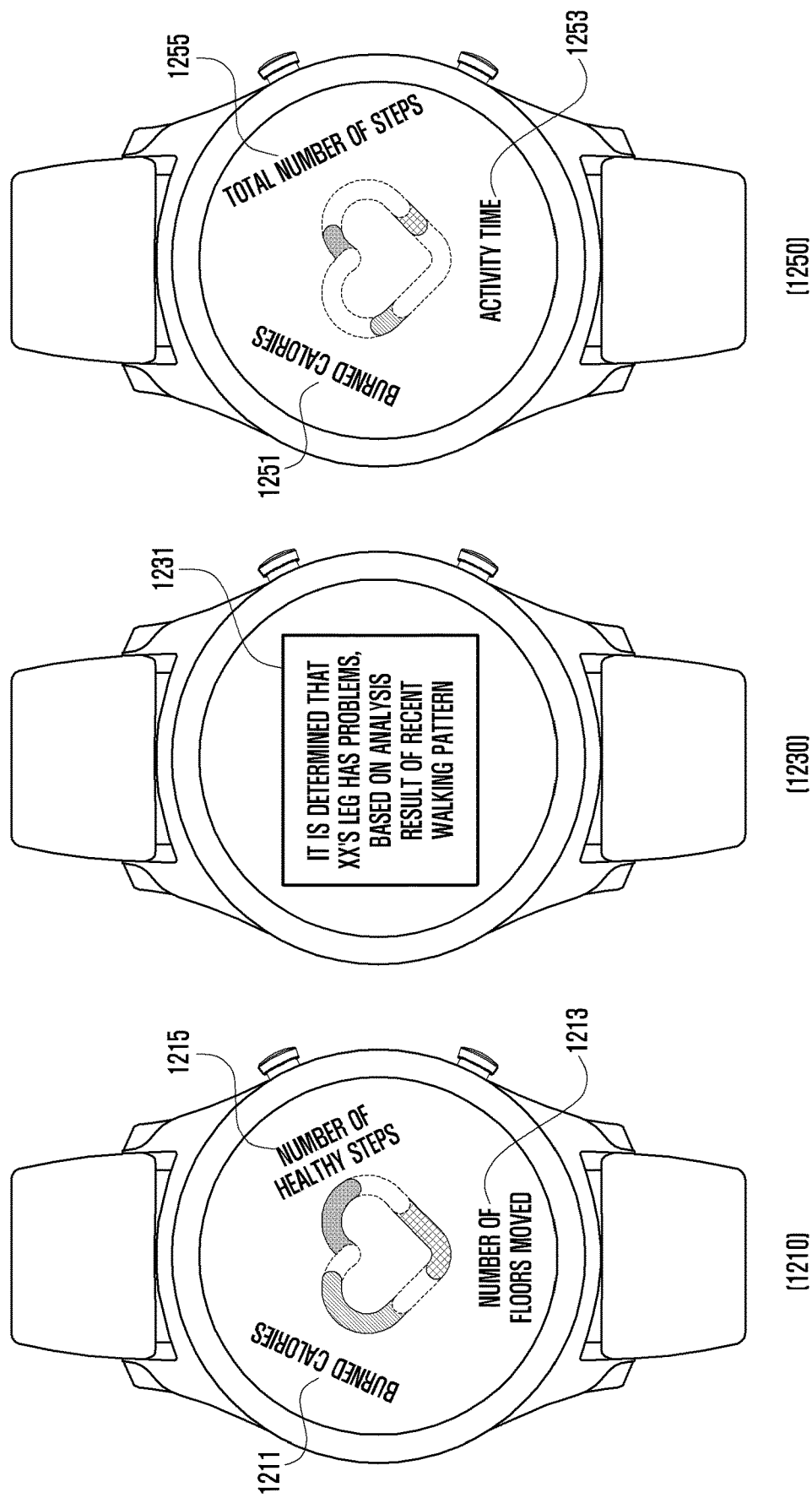

FIGS. 10 to 12 are diagrams illustrating examples in which an electronic device displays activity information according to an operation mode according to various different embodiments.

FIG. 10 illustrates an example of differently indicating activity information according to the operation mode.

Referring to FIG. 10, when the first operation mode is configured, a processor (for example, the processor 120 of FIG. 1) of an electronic device (for example, the electronic device 101 of FIG. 1) may provide first activity information. The first activity information 1010 may include at least one of burned calories 1011, the number of floors 1013 moved, or the number of healthy steps 1015. The first activity information 1010 may be displayed in a heart shape, and each of a satisfaction value of the activity information and a target value of the activity information may be displayed in the activity information. The processor 120 may display the target value more faintly than the satisfaction value. When the second operation mode or the third operation mode is configured, the processor 120 may provide the second activity information 1030. The second activity information 1030 may include at least one of the burned calories 1031, the activity time 1033, or the total number of steps 1035. As the second activity information 1030, the activity time 1033 or the total number of steps 1035 may be displayed differently from the first activity information 1010. When the fourth operation mode is configured, the processor 120 may provide third activity information 1050. The third activity information 1050 may include at least one of the burned calories 1051, the ascended height 1053, or the total number of strokes 1055. As the third activity information 1050, the ascended height 1053 or the total number of strokes 1055 may be displayed differently from the first activity information 1010 or the second activity information 1030.

FIG. 11 illustrates an example of differently displaying activity information according to a movement characteristic change.

Referring to FIG. 11, a processor (for example, the processor 120 of FIG. 1) of an electronic device (for example, the electronic device 101 of FIG. 1) may provide at least one piece of first activity information 1110, second activity information 1130, or third activity information 1150. The processor 120 may sequentially provide the first activity information 1110, the second activity information 1130, or the third activity information 1150 according to a movement characteristic change. The first activity information 1110 or the third activity information 1150 may be displayed in a heart shape, and each of satisfaction values of the activity information and target values of the activity information may be displayed on the basis of the activity information. The processor 120 may display the target value more faintly than the satisfaction value.

For example, when the user injures his/her leg and thus a walking pattern (or step pattern) is changed, the processor 120 may provide the first activity information 1110. The first activity information 1110 may include at least one of burned calories 1111, activity time 1113, or the total number of steps 1115. The processor 120 may analyze the user's walking pattern and provide the second activity information 1130. The second activity information 1130 may inform that the user's walking pattern is recovering to healthy walking. The second activity information 1130 may include at least one of text, images, or videos. The second activity information 1130 may be displayed in a popup while overlapping the first activity information 1110. After providing the second activity information 1130, the processor 120 may provide the third activity information 1150. The third activity information 1150 may include at least one of the burned calories 1151, the number of floors 1153 moved, or the number of healthy steps 1155. When the injured leg of the user is recovered and thus the user walks normally for a predetermined time (for example, 5 minutes or 10 minutes), the processor 120 may provide the step of healthy steps 1155 instead of the total number of steps (for example, the total number of steps 1115 in the first activity information 1110). Further, when the injured leg of the user is recovered and thus the user can climb stairs, the processor 120 may provide the number of floors 1153 moved instead of the activity time (for example, the activity time 1113 in the first activity information 1110) as the activity information.

According to an embodiment, when providing the first activity information 1110, the second activity information 1130, or the third activity information 1150, the electronic device 101 may be configured to be in the first operation mode. The processor 120 may only display different activity information according to the walking pattern but may not change the operation mode of the electronic device 101. Alternatively, the processor 120 may configure the electronic device 101 to be in the second operation mode when providing the first activity information 1110 and the second activity information 1130 and may switch (or change) the second operation mode to the first operation mode when providing the third activity information 1150. The processor 120 may differently display activity information according to the walking pattern and change the operation mode of the electronic device 101. Alternatively, when providing the third activity information 1150, the processor 120 may recommend switching the electronic device 101 from the second operation mode to the first operation mode. The processor 120 may or may not change the operation mode of the electronic device 101 on basis of a user selection for the recommendation.

FIG. 12 illustrates an example of differently displaying activity information according to a movement characteristic change.

Referring to FIG. 12, when the first operation mode is configured, a processor (for example, the processor 120 of FIG. 1) of an electronic device (for example, the electronic device 101 of FIG. 1) may provide at least one piece of first activity information 1210, second activity information 1230, or third activity information 1250. The processor 120 may sequentially provide the first activity information 1210, the second activity information 1230, or the third activity information 1250 according to a movement characteristic change. The first activity information 1210 or the third activity information 1250 may be displayed in a heart shape, and each of satisfaction values of the activity information and target values of the activity information may be displayed on the basis of the activity information. The processor 120 may display the target value more faintly than the satisfaction value.

For example, the processor 120 may provide the first activity information 1210 for a user having no difficulty in walking. The first activity information 1210 may include at least one of the burned calories 1211, the number of floors 1213 moved, or the number of healthy steps 1215. The processor 120 may analyze the user's walking pattern and provide the second activity information 1230. The second activity information 1230 may inform that the user previously having no difficulty in walking has injured his/her leg and thus a walking pattern is changed. The second activity information 1230 may include at least one of text, images, or videos. The second activity information 1230 may be displayed in a popup while overlapping the first activity information 1210. After providing the second activity information 1230, the processor 120 may provide the third activity information 1250. The third activity information 1250 may include at least one of burned calories 1251, activity time 1253, or the total number of steps 1255. When the user previously having no difficulty in walking injures his/her leg and thus cannot walk continuously for a predetermined time (for example, 5 minutes or 10 minutes), the processor 120 may provide the total number of steps 1255 instead of the number of healthy steps (for example, the number of healthy steps 1215 in the first activity information 1210) as the activity information. Further, when the user injures his/her leg and thus cannot climb stairs, the processor 120 may provide the activity time 1253 instead of the number of floors 1213 moved (for example, the number of floors 1213 climbed or descended in the first activity information 1210).

According to an embodiment, when providing the first activity information 1210, the second activity information 1230, or the third activity information 1250, the electronic device 101 may be configured to be in the first operation mode. The processor 120 may only display different activity information according to the walking pattern but may not change the operation mode of the electronic device 101. Alternatively, the processor 120 may configure the electronic device 101 to be in the first operation mode when providing the first activity information 1210 and the second activity information 1230 and may switch (or change) the first operation mode to the second operation mode when providing the third activity information 1250. The processor 120 may differently display activity information according to the walking pattern and change the operation mode of the electronic device 101. When providing the third activity information 1250, the processor 120 may recommend switching the electronic device 101 from the first operation mode to the second operation mode. The processor 120 may or may not change the operation mode of the electronic device 101 on basis of a user selection for the recommendation.

Figure 13:
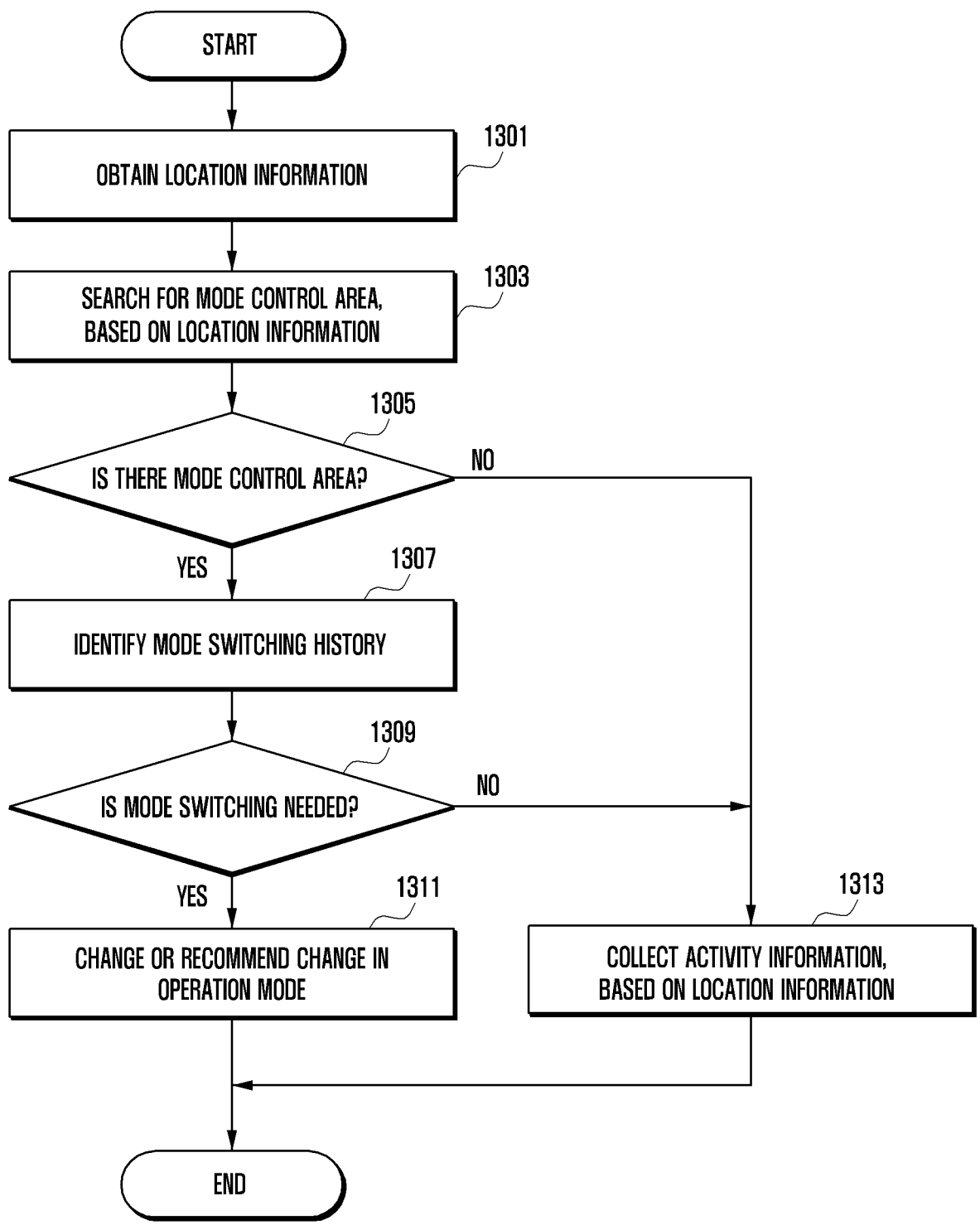
FIG. 13 is a flowchart 1300 illustrating a method by an electronic device controls an operation mode on the basis of location information according to an embodiment.

FIG. 13 is a flowchart 1300 illustrating a method by an electronic device controls an operation mode on the basis of location information according to an embodiment.

Referring to FIG. 13, in operation 1301, a processor (for example, the processor 120 of FIG. 1) of an electronic device (for example, the electronic device 101 of FIG. 1) may obtain location information. The location information (e.g. current location information) may be obtained from a communication module (for example, the communication module 190 of FIG. 1). The location information may be GPS information or wifi information. The processor 120 may analyze the location information on the basis of wifi information to which the electronic device 101 is connected. The processor 120 may periodically or selectively obtain the location information. For example, when an operation mode change according to the location is enabled by the user in advance or by default in the electronic device 101, the processor 120 may obtain the location information. When the operation mode change according to the location is not enabled in the electronic device 101, the processor 120 may not obtain the location information.

In operation 1303, the processor 120 may search for a mode control area on the basis of the location information. The mode control area may mean that the operation mode of the electronic device 101 is differently configured in accordance with the location information. The mode control area may be configured by the user or the electronic device 101. The processor 120 may configure the mode control area on the basis of a user input. For example, the user using crutches may configure the electronic device 101 to be in the first operation mode at home, configure the electronic device 101 to be in the fourth operation mode in an office, and configure the electronic device 101 to be in the second operation mode while moving from the home to the office. The user may differently configure the operation mode of the electronic device 101 according to the location corresponding to the home, the location corresponding to the office, or the location while commuting. Alternatively, the user having no difficulty in walking may configure the electronic device 101 to be in the first operation mode regardless of the location. Alternatively, a disabled user may configure the electronic device 101 to be in one of the second operation mode, the third operation mode, or the fourth operation mode regardless of the location.

According to an embodiment, the processor 120 may store location information having the operation mode changed by the user in a memory (for example, the memory 130). The processor 120 may configure the mode control area on the basis of location information by performing clustering on the basis of location information for a predetermined time. When the mode control area is configured, it may be stored in the memory (for example, the memory 130).

In operation 1305, the processor 120 may identify (or determine) whether there is the mode control area. The processor 120 may identify whether the mode control area is configured by the user. The processor 120 may perform operation 1307 when there is the mode control area and perform operation 1313 when there is no mode control area.

When there is the mode control area, the processor 120 may identify a mode switching history in operation 1307. The mode switching history may indicate whether the operation mode has been switched directly by the user of the electronic device 101 or switched automatically by the electronic device 101 for the mode control area. The processor 120 may identify the mode switching history for a recent predetermined time (for example, one week, half month, or one month).

In operation 1309, the processor 120 may identify (or determine) whether switching of the operation mode of the electronic device 101 is needed on the basis of the mode switching history. When there is the mode control area corresponding to the location information but the operation mode is not changed for the location information for the preceding week, the processor 120 may determine that mode switching is not needed. Alternatively, when the number of times of entering the location information corresponding to the mode control area for a recent predetermined period is equal to or smaller than a reference number, the processor 120 may determine that mode switching is not needed. Alternatively, when the number of times of entering the location information corresponding to the mode control area for a recent predetermined period exceeds the reference number, the processor 120 may determine that mode switching is needed.

The processor 120 may perform operation 1311 when it is determined that mode switching is needed and perform operation 1313 when it is determined that mode switching is not needed.

When the mode switching is needed, the processor 120 may change or recommend the change of the operation mode of the electronic device 101 in operation 1311. For example, when the current location information is the location corresponding to an office, the processor 120 may automatically switch to the fourth operation mode or propose the change to the fourth operation mode.

When there is no mode control area or the mode switching is not needed, the processor 120 may collect activity information on the basis of location information in operation 1313. When there is mode control area, the processor 120 may collect activity information on the basis of location information. Further, the processor 120 may configure the mode control area on the basis of location information by performing clustering on the basis of the location information. When the number of times of entering the location information corresponding to the mode control area for a recent predetermined period is equal to or smaller than the reference number, the processor 120 may delete the mode control area.

A method of operating an electronic device (for example, the electronic device 101 of FIG. 1) according to an embodiment may include an operation of acquiring sensing data from a sensor module of the electronic device, an operation of analyzing a movement pattern of a user on the basis of the acquired sensing data, an operation of estimating movement characteristic information on the basis of a result of the analysis of the movement pattern, an operation of identifying an operation mode of the electronic device on the basis of the movement characteristic information, and an operation of analyzing activity information of the user on the basis of the identified operation mode to display the activity information using a display of the electronic device.

The movement pattern may include a walking pattern or a stroke pattern, and the operation of analyzing may include an operation of extracting a pattern characteristic from the sensing data obtained for a predetermined time and an operation of identifying whether the extracted pattern characteristic corresponds to at least one of the walking pattern or the stroke pattern.

The operation of identifying may include an operation of analyzing a walking pattern from the sensing data, an operation of calculating a left/right symmetry level of walking, an up/down symmetry level, or a regularity level on the basis of a result of the analysis, and an operation of identifying the operation mode of the electronic device on the basis of at least one of the calculated left/right symmetry level, up/down symmetry level, or regularity level.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

Various embodiments of the disclosure disclosed in the specifications and drawings present specific examples for ease of description of the technical content of the disclosure and to help understanding of the disclosure, but are not intended to limit the scope of the disclosure. Therefore, it should be construed that not only the embodiments disclosed herein but also all modifications or modified forms capable of being derived on the basis of the technical idea of the disclosure are included in the scope of the disclosure.

The invention claimed is:

1. An electronic device comprising:
a sensor module;
a display;
a communication module;
memory storing instructions; and
a processor, wherein the instructions that, when executed by the processor, cause the electronic device to:
obtain sensing data from the sensor module;
analyze a movement pattern of a user including a walking pattern or a stroke pattern based on the obtained sensing data;
identify an operation mode of the electronic device as a first operation mode when the movement pattern of the user is analyzed as the walking pattern;
identify whether there is a connection with an external device corresponding to a walking assist device through the communication module,
identify the operation mode of the electronic device as a second operation mode when there is no connection with the external device,
identify the operation mode of the electronic device as a third operation mode when there is the connection with the external device; and
analyze activity information of the user based on the identified operation mode to display the activity information using the display.

2. The electronic device of claim 1, wherein the instructions, when executed by the processor, cause the electronic device to:
extract a pattern characteristic from the sensing data obtained for a predetermined time and identify whether the extracted pattern characteristic corresponds to at least one of the walking pattern or the stroke pattern.

3. The electronic device of claim 1, wherein the instructions, when executed by the processor, cause the electronic device to calculate a left/right symmetry level, an up/down symmetry level, or a regularity level by analyzing the walking pattern and identify the operation mode of the electronic device as at least one the first operation mode, the second operation mode, or the third operation mode, based on at least one of the calculated left/right symmetry level, up/down symmetry level, and/or regularity level.

4. The electronic device of claim 3, wherein, when the left/right symmetry level, the up/down symmetry level, or the regularity level exceeds a reference value, the instructions, when executed by the processor, cause the electronic device to identify the operation mode of the electronic device as the first operation mode.

5. The electronic device of claim 3, wherein, when the left/right symmetry level, the up/down symmetry level, or the regularity level is equal to or smaller than a reference value, the instructions, when executed by the processor, cause the electronic device to identify the operation mode of the electronic device as the second operation mode or the third operation mode.

6. The electronic device of claim 1, wherein the instructions, when executed by the processor, cause the electronic device to calculate at least one of a Ground Contact Time (GCT) signal, x, y, and z values of an acceleration signal, and/or an acceleration variance value from the obtained sensing data, and analyze the movement pattern, based on at least one of the calculated GCT signal, the x, y, and z values of the acceleration signal, and/or the acceleration variance value.

7. The electronic device of claim 6, wherein the instructions, when executed by the processor, cause the electronic device to identify at least one of symmetry, regularity, and/or undulation, based on at least one of the GCT signal, the x, y, and z values of the acceleration signal, and/or the acceleration variance value.

8. The electronic device of claim 1, wherein the instructions, when executed by the processor, cause the electronic device to control a function engine, based on the identified operation mode and collect the activity information using the function engine.

9. The electronic device of claim 1, wherein the instructions, when executed by the processor, cause the electronic device to determine different parameters for different operation modes of the electronic device and apply a parameter corresponding to the identified operation mode to the activity information.

10. The electronic device of claim 1, wherein the instructions, when executed by the processor, cause the electronic device to analyze a change in a walking pattern of the user, based on the obtained sensing data and display different pieces of activity information according to the change in the walking pattern.

11. The electronic device of claim 1, wherein the instructions, when executed by the processor, cause the electronic device to:
based on location information of the electronic device for a predetermined time, configure a mode control area corresponding to the location information, and
store the configured mode control area in the memory.

12. The electronic device of claim 11, wherein the instructions, when executed by the processor, cause the electronic device to change the operation mode of the electronic device corresponding to the location information, based on at least one of the mode control area stored in the memory and/or a mode switching history.

13. A method of operating an electronic device comprising:
acquiring sensing data from a sensor module of the electronic device;
analyzing a movement pattern of a user, based on the acquired sensing data;
identifying an operation mode of the electronic device, as a first operation mode when the movement pattern of the user is analyzed as walking pattern;
identifying whether there is a connection with an external device corresponding to a walking assist device through a communication module,
identifying the operation mode of the electronic device as a second operation mode when there is no connection with the external device,
identifying the operation mode of the electronic device as a third operation mode when there is the connection with the external device; and
analyzing activity information of the user, based on the identified operation mode to display the activity information using a display of the electronic device.

* * * * *